(12) United States Patent
Dahmen et al.

(10) Patent No.: US 8,765,636 B2
(45) Date of Patent: Jul. 1, 2014

(54) SYNERGISTIC FUNGICIDAL ACTIVE COMPOUND COMBINATIONS CONTAINING A CARBOXAMIDE, AN AZOLE, A SECOND AZOLE OR A STROBILURIN

(75) Inventors: Peter Dahmen, Neuss (DE); Ulrike Wachendorff-Neumann, Neuwied (DE); Isolde Häuser-Hahn, Leverkusen (DE); Hans-Ludwig Elbe, Wuppertal (DE); Ralf Dunkel, Lyons (FR); Anne Suty-Heinze, Langenfeld (FR)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

(21) Appl. No.: 13/597,786

(22) Filed: Aug. 29, 2012

(65) Prior Publication Data

US 2013/0053241 A1 Feb. 28, 2013

Related U.S. Application Data

(63) Continuation of application No. 13/100,464, filed on May 4, 2011, now abandoned, which is a continuation of application No. 11/997,079, filed as application No. PCT/EP2006/006932 on Jul. 15, 2006, now abandoned.

(30) Foreign Application Priority Data

Jul. 28, 2005 (DE) .......................... 10 2005 035 300

(51) Int. Cl.
*A01N 25/26* (2006.01)
*A01N 43/707* (2006.01)
*A01N 43/64* (2006.01)
*A01N 43/56* (2006.01)
*A01P 3/00* (2006.01)

(52) U.S. Cl.
USPC ........ 504/100; 514/229.2; 514/383; 514/384; 514/406

(58) Field of Classification Search
USPC ................. 504/100; 514/229.2, 383, 384, 406
See application file for complete search history.

(56) References Cited

U.S. PATENT DOCUMENTS

| | | |
|---|---|---|
| 3,912,752 A | 10/1975 | Meiser et al. |
| 3,952,002 A | 4/1976 | Kramer et al. |
| 4,079,062 A | 3/1978 | Van Reet et al. |
| 4,245,432 A | 1/1981 | Dannelly |
| 4,272,417 A | 6/1981 | Barke et al. |
| 4,432,989 A | 2/1984 | Spencer |
| 4,496,551 A | 1/1985 | Moberg |
| 4,532,341 A | 7/1985 | Holmwood et al. |
| 4,551,469 A | 11/1985 | Parry et al. |
| 4,598,085 A | 7/1986 | Heeres et al. |
| 4,652,580 A | 3/1987 | Janssen et al. |
| 4,664,696 A | 5/1987 | Schaub |
| 4,731,106 A | 3/1988 | Green et al. |
| 4,808,430 A | 2/1989 | Kouno |
| 4,829,085 A | 5/1989 | Wenderoth et al. |
| 4,851,405 A | 7/1989 | Krámer et al. |
| 4,877,441 A | 10/1989 | Mori et al. |
| 4,920,139 A | 4/1990 | Fujimoto |
| 5,021,581 A | 6/1991 | Clough et al. |
| 5,081,141 A | 1/1992 | Colle et al. |
| 5,087,635 A | 2/1992 | Shaber |
| 5,145,856 A | 9/1992 | Clough et al. |
| 5,185,342 A | 2/1993 | Hayase et al. |
| 5,221,691 A | 6/1993 | Clough et al. |
| 5,256,683 A | 10/1993 | Hutt et al. |
| 5,266,585 A | 11/1993 | Hubele et al. |
| 5,306,712 A | 4/1994 | Tobitsuka et al. |
| 5,407,902 A | 4/1995 | Oda et al. |
| 5,679,676 A | 10/1997 | Krüger et al. |
| 5,747,518 A | 5/1998 | Yoshikawa et al. |
| 5,789,430 A | 8/1998 | Jautelat et al. |
| 5,869,517 A | 2/1999 | Müller et al. |
| 5,876,739 A | 3/1999 | Turnblad et al. |
| 5,914,344 A | 6/1999 | Yoshikawa et al. |
| 5,948,932 A | 9/1999 | Grote et al. |
| 5,998,450 A | 12/1999 | Eicken et al. |
| 6,103,717 A | 8/2000 | Heinemann et al. |
| 6,169,056 B1 | 1/2001 | Bayer et al. |
| 6,191,128 B1 | 2/2001 | Stenzel et al. |
| 6,350,765 B1 | 2/2002 | Schelberger et al. |

(Continued)

FOREIGN PATENT DOCUMENTS

| | | |
|---|---|---|
| CA | 2476462 A1 * | 8/2003 |
| CA | 2 543 053 A1 | 5/2005 |

(Continued)

OTHER PUBLICATIONS

Bauer, T.A., et al., "Response of Selected Weed Species to Postemergence Imazethapyr and Bentazon," *Weed Tech.* 9:236-242, The Weed Science Society of America, United States (1995).

Blackshaw, R.E., "HOE-39866 Use in Chemical Fallow Systems," *Weed Tech.* 3:420-428, The Weed Science Society of America, United States (1989).

Blackshaw, R.E., "Synergistic Mixes of DPX-A7881 and Clopyralid in Canola (*Brassica napus*)," *Weed Tech.* 3:690-695, The Weed Science Society of America, United States (1989).

Blackshaw, R.E., et al., "Herbicide Combinations for Postemergent Weed Control In Safflower (*Carthamus tinctorius*)," *Weed Tech.* 4:97-104, The Weed Science Society of America, United States (1990).

Blouin, D.C., et al., "Analysis of Synergistic and Antagonistic Effects of Herbicides Using Nonlinear Mixed-Model Methodology," *Weed Tech.* 18:464-472, The Weed Science Society of America, United States (2004).

(Continued)

*Primary Examiner* — John Pak
*Assistant Examiner* — Andriae M Holt
(74) *Attorney, Agent, or Firm* — Sterne, Kessler, Goldstein & Fox P.L.L.C.

(57) ABSTRACT

The present invention relates to novel active compound combinations comprising a known carboxamide, a known azole and additionally a second known azole or alternatively a known strobilurin, which combinations are highly suitable for controlling unwanted phytopathogenic fungi.

9 Claims, No Drawings

(56) References Cited

U.S. PATENT DOCUMENTS

| | | | |
|---|---|---|---|
| 6,355,634 | B1 | 3/2002 | Isenring et al. |
| 7,329,633 | B2 | 2/2008 | Dunkel et al. |
| 7,358,214 | B2 | 4/2008 | Dunkel et al. |
| 7,521,397 | B2 | 4/2009 | Dunkel et al. |
| 7,538,073 | B2 | 5/2009 | Elbe et al. |
| 7,799,739 | B2 | 9/2010 | Dunkel et al. |
| 7,820,708 | B2 | 10/2010 | Dunkel et al. |
| 7,879,760 | B2 | 2/2011 | Dunkel et al. |
| 8,431,600 | B2 | 4/2013 | Dunkel et al. |
| 2001/0018442 | A1 | 8/2001 | Gayer et al. |
| 2002/0115564 | A1 | 8/2002 | Asrar et al. |
| 2002/0134012 | A1 | 9/2002 | Ding et al. |
| 2002/0173529 | A1 | 11/2002 | Dutzmann et al. |
| 2003/0176428 | A1 | 9/2003 | Schneidersmann et al. |
| 2004/0039043 | A1 | 2/2004 | Elbe et al. |
| 2004/0204470 | A1 | 10/2004 | Elbe et al. |
| 2005/0119130 | A1 | 6/2005 | Walter |
| 2005/0124815 | A1 | 6/2005 | Elbe et al. |
| 2006/0014738 | A1* | 1/2006 | Wachendorff-Neumann et al. ............ 514/229.2 |
| 2006/0089399 | A1 | 4/2006 | Dunkel et al. |
| 2006/0116414 | A1 | 6/2006 | Dunkel et al. |
| 2006/0211771 | A1 | 9/2006 | Elbe et al. |
| 2007/0037799 | A1 | 2/2007 | Dahmen et al. |
| 2007/0060579 | A1 | 3/2007 | Wachendorff-Neumann et al. |
| 2007/0196406 | A1 | 8/2007 | Dunkel et al. |
| 2008/0113979 | A1 | 5/2008 | Foor |
| 2008/0255071 | A1 | 10/2008 | Suty-Heinze et al. |
| 2009/0018015 | A1 | 1/2009 | Wachendorff-Neumann et al. |
| 2009/0069398 | A1 | 3/2009 | Dunkel et al. |
| 2009/0105311 | A1 | 4/2009 | Dunkel et al. |
| 2009/0118346 | A1 | 5/2009 | Dunkel et al. |
| 2009/0286681 | A1 | 11/2009 | Dahmen et al. |
| 2011/0218100 | A1 | 9/2011 | Dahman et al. |
| 2012/0015910 | A1 | 1/2012 | Wachendorff-Neumann et al. |

FOREIGN PATENT DOCUMENTS

| | | |
|---|---|---|
| DE | 2 201 063 A1 | 7/1973 |
| DE | 25 51 560 C3 | 4/1981 |
| DE | 30 42 303 A1 | 8/1981 |
| DE | 23 24 010 C3 | 10/1981 |
| DE | 37 21 786 A1 | 1/1988 |
| DE | 27 35 872 C2 | 10/1989 |
| DE | 34 06 993 C2 | 2/1990 |
| DE | 44 23 612 A1 | 1/1996 |
| DE | 195 31 813 A1 | 3/1997 |
| DE | 195 39 324 A1 | 4/1997 |
| DE | 196 02 095 A1 | 7/1997 |
| DE | 196 46 407 A1 | 5/1998 |
| EP | 0 015 756 B1 | 5/1983 |
| EP | 0 112 284 A2 | 6/1984 |
| EP | 0 040 345 B1 | 7/1984 |
| EP | 0 068 813 B1 | 9/1985 |
| EP | 0 258 161 A2 | 3/1988 |
| EP | 0 183 458 B1 | 6/1989 |
| EP | 0 145 294 B1 | 10/1989 |
| EP | 0 253 213 B1 | 3/1990 |
| EP | 0 281 842 B1 | 7/1991 |
| EP | 0 234 242 B1 | 8/1991 |
| EP | 0 196 038 B1 | 1/1992 |
| EP | 0 278 595 B1 | 11/1992 |
| EP | 0 315 502 B1 | 6/1993 |
| EP | 0 329 397 B1 | 10/1993 |
| EP | 0 382 375 B1 | 3/1994 |
| EP | 0 378 953 B1 | 5/1996 |
| EP | 0 569 384 B1 | 7/1996 |
| EP | 0 398 692 B1 | 8/1996 |
| EP | 0 460 575 B1 | 9/1996 |
| EP | 0 537 957 B1 | 2/1997 |
| EP | 0 596 254 B1 | 6/1997 |
| EP | 0 712 396 B1 | 11/1998 |
| EP | 0 737 682 B1 | 1/2002 |
| EP | 0 975 219 B1 | 3/2002 |
| EP | 0 944 318 B1 | 4/2003 |
| JP | 10-251240 A | 9/1998 |
| JP | 10-310577 A | 11/1998 |
| WO | WO 96/16048 A1 | 3/1996 |
| WO | WO 97/10716 A1 | 3/1997 |
| WO | WO 98/23155 A1 | 6/1998 |
| WO | WO 99/31979 A1 | 7/1999 |
| WO | WO 02/08197 A1 | 1/2002 |
| WO | WO 02/28186 A2 | 4/2002 |
| WO | WO 02/38542 A1 | 5/2002 |
| WO | WO 02/080675 A1 | 10/2002 |
| WO | WO 03/010149 A1 | 2/2003 |
| WO | WO 03/066610 A1 | 8/2003 |
| WO | WO 03/070705 A1 | 8/2003 |
| WO | WO 2004000022 A1 * | 12/2003 |
| WO | WO 2004/005242 A1 | 1/2004 |
| WO | WO 2004/067515 A1 | 8/2004 |
| WO | WO 2005/011379 A1 | 2/2005 |
| WO | WO 2005/034628 A1 | 4/2005 |
| WO | WO 2005/041653 A2 | 5/2005 |
| WO | WO 2006/036827 A1 | 4/2006 |
| WO | WO 2007/003643 A1 | 1/2007 |

OTHER PUBLICATIONS

Bradley, P.R., et al., "Response of Sorghum (*Sorghum bicolor*) to Atrazine, Ammonium Sulfate, and Glyphosate," *Weed Tech.* 14:15-18, The Weed Science Society of America, United States (2000).

Buker, III, R.S., et al., "Confirmation and Control of a Paraquat-Tolerant Goosegrass (*Eleusine indica*) Biotype," *Weed Tech.* 16:309-313, The Weed Science Society of America, United States (2002).

Burke, I.C., et al., "CGA-362622 Antagonizes Annual Grass Control with Clethodim," *Weed Tech.* 16:749-754, The Weed Science Society of America, United States (2002).

Colby, S.R., "Calculating Synergistic and Antagonistic Responses of Herbicide Combinations," *Weeds* 15:20-22, Weed Society of America, United States (1967).

FLint, J.L., et al., "Analyzing Herbicide Interactions: A Statistical Treatment of Colby's Method," *Weed Tech.* 2:304-309, The Weed Science Society of America, United States (1988).

Gillespie, G.R., and Nalewaja, J.D., "Wheat (*Triticum aestivum*) Response to Triallate Plus Chlorsulfuron," *Weed Tech.* 3:20-23, The Weed Science Society of America, United States (1989).

Green, J.M., et al., "Metribuzin and Chlorimuron Mixtures for Preemergence Broadleaf Weed Control in Soybeans, *Glycine max*," *Weed Tech.* 2:355-363, The Weed Science Society of America, United States (1988).

Harker, K.N., and O'Sullivan, P.A., "Synergistic Mixtures of Sethoxydim and Fluazifop on Annual Grass Weeds," *Weed Tech.* 5:310-316, The Weed Science Society of America, United States (1991).

Kent, L.M., et al., "Effect of Ammonium Sulfate, Imazapyr, and Environment on the Phytotoxicity of Imazethapyr," *Weed Tech.* 5:202-205, The Weed Science Society of America, United States (1991).

Kotoula-Syka, E., et al., "Interactions Between SAN 582H and Selected Safeners on Grain Sorghum (*Sorghum bicolor*) and Corn (*Zea mays*)," *Weed Tech.* 10:299-304, The Weed Science Society of America, United States (1996).

Lanclos, D.Y., et al., "Glufosinate Tank-Mix Combinations in Glufosinate-Resistant Rice (*Oryza sativa*)," *Weed Tech.* 16:659-663, The Weed Science Society of America, United States (2002).

Norris, J.L., et al., "Weed Control from Herbicide Combinations with Three.Formulations of Glyphosate," *Weed Tech.* 15:552-558, The Weed Science Society of America, United States (2001).

Novosel, K.M., et al., "Metolachlor Efficacy as Influenced by Three Acetolactate Synthase-Inhibiting Herbicides," *Weed Tech.* 12:248-253, The Weed Science Society of America, United States (1998).

Palmer, E. W., et aL, "Broadleaf Weed Control in Soybean (*Glycine max*) with CGA-277476 and Four Postemergence Herbicides," *Weed Tech.* 14:617-623, The Weed Science Society of America, United States (2000).

Rummens, F.H.A., "An Improved Definition of Synergistic and Antagonistic Effects," *Weed Science* 23:4-6, The Weed Science Society of America, United States (1975).

(56) References Cited

OTHER PUBLICATIONS

Salzman, F.P., and Renner, K.A., "Response of Soybean to Combinations of Clomazone, Metribuzin, Linuron, Alachlor, and Atrazine," *Weed Tech.* 6:922-929, The Weed Science Society of America, United States (1992).

Scott, R.C., et al., "Spray Adjuvant, Formulation, and Environmental Effects on Synergism from Post-Applied Tank Mixtures of SAN 582H with Fluazifop-P, Imazethapyr, and Sethoxydim," *Weed Tech.* 12:463-469, The Weed Science Society of America, United States (1998).

Shaw, D.R., and Arnold, J.C., "Weed Control from Herbicide Combinations with Glyphosate," *Weed Tech.* 16:1-6, The Weed Science Society of America, United States (2002).

Snipes, C.F., and Allen, R.L., "Interaction of Graminicides Applied in Combination with Pyrithiobac," *Weed Tech.* 10:889-892, The Weed Science Society of America, United States (1996).

Sun, Y.-P., et al., "Analysis of Joint Action of Insecticides Against House Flies," *J. Econ. Entomol.* 53:887-892, Entomological Society of America, United States (1960).

Tammes, P.M.L., "Isoboles, A Graphic Representation of Synergism in Pesticides," *Neth. J. Plant Path.* 70:73-80, Springer, Germany (1964).

Wehtje, G., and Walker, R.H., "Interaction of Glyphosate and 2,4-DB for the Control of Selected Morninglory (*Ipomoea* spp.) Species," *Weed Tech.* 11:152-156, The Weed Science Society of America, United States (1997).

Zhang, W., et al., "Fenoxaprop Interactions for Barnyardgrass (*Echinochloa crus-galli*) Control in Rice," *Weed Tech.* 19:293-297, The Weed Science Science Society of America, United States (2005).

International Search Report for International Application No. PCT/EP2006/006932, European Patent Office, Netherlands, mailed on Feb. 15, 2007.

Office Action dated Jul. 18, 2011, in U.S. Appl. No. 11/916,436, Dunkel, R. et al., filed Nov. 7, 2008.

English language Abstract of European European Patent Application No. EP 0 258 161 A2, European Patent Office, espacenet database—Worldwide (2001).

Office Action mailed Apr. 15, 2013, in U.S. Appl. No. 13/242,052, inventors Wachendorff-Neumann et al., filed Sep. 23, 2011.

Office Action dated Jan. 30, 2012, in U.S. Appl. No. 11/916,436, Dunkel, R. et al., filed Nov. 7, 2008.

Office Action dated Aug. 1, 2012, in U.S. Appl. No. 11/916,436, Dunkel, R. et al., filed Nov. 7, 2008.

Office Action mailed Oct. 11, 2013, in U.S. Appl. No. 13/242,052, inventors Wachendorff-Neumann et al., filed Sep. 23, 2011.

\* cited by examiner

SYNERGISTIC FUNGICIDAL ACTIVE COMPOUND COMBINATIONS CONTAINING A CARBOXAMIDE, AN AZOLE, A SECOND AZOLE OR A STROBILURIN

The present invention relates to novel active compound combinations comprising a known carboxamide, a known azole and additionally a second known azole or alternatively a known strobilurin, which combinations are highly suitable for controlling unwanted phytopathogenic fungi.

It is already known that certain carboxamides, such as, for example, N-[2-(1,3-dimethylbutyl)phenyl]-5-fluoro-1,3-dimethyl-1H-pyrazole-4-carboxamide and N-(3',4'-dichloro-5-fluoro-1,1'-biphenyl-2-yl)-3-(difluoromethyl)-1-methyl-1H-pyrazole-4-carboxamide, certain azoles, such as, for example, 1-(4-chlorophenyl)-4,4-dimethyl-3-(1H-1,2,4-triazol-1-ylmethyl)pentan-3-ol (tebuconazole) and 2-[2-(1-chlorocyclopropyl)-3-(2-chlorophenyl)-2-hydroxypropyl]-2,4-dihydro-3H-1,2,4-triazole-3-thione (prothioconazole), and also certain strobilurins, such as, for example, methyl α-(methoxyimino)-2-[[[[1-[3-(trifluoromethyl)phenyl]ethylidene]amino]oxy]methyl]benzeneacetate (trifloxystrobin) and (1E)-[2-[[6-(2-chlorophenoxy)-5-fluoro-4-pyrimidinyl]oxy]phenyl](5,6-dihydro-1,4,2-dioxazin-3-yl)methanone O-methyloxime (fluoxastrobin) have fungicidal properties (cf. DE-A 196 02 095, EP-A 0 281 842, EP-A 0 040 345, EP-A 0 460 575, WO 96/16048, WO 03/010149 and WO 03/070705).

Furthermore, it is known that mixtures of carboxamides and azoles or strobilurins or of azoles and strobilurins or mixtures of one strobilurin with two azoles can be used for controlling fungi in crop protection (cf. WO 2005/011379, WO 2005/034628, WO 2005/041653, EP-A-0 944 318, EP-A-0 975 219).

Both the activity of the individual components and the activity of the known mixtures of in each case two or three active compounds is good; however, it is sometimes unsatisfactory.

This invention now provides novel active compound combinations having very good fungicidal properties, comprising (A) a carboxamide of the general formula (I)

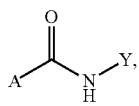

(I)

in which
A represents one of the radicals A1 to A8 below:

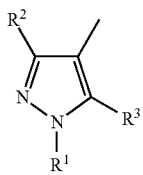

A1

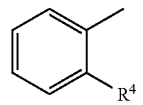

A2

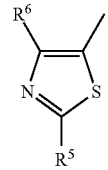

A3

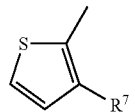

A4

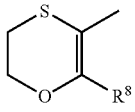

A5

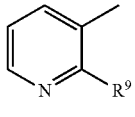

A6

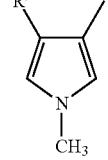

A7

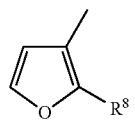

A8

$R^1$ represents methyl, ethyl, n- or isopropyl,
$R^2$ represents iodine, methyl, difluoromethyl or trifluoromethyl,
$R^3$ represents hydrogen, fluorine, chlorine or methyl,
$R^4$ represents chlorine, bromine, iodine, methyl, difluoromethyl or trifluoromethyl,
$R^5$ represents hydrogen, chlorine, methyl, amino or dimethylamino,
$R^6$ represents methyl, difluoromethyl or trifluoromethyl,
$R^7$ represents bromine or methyl,
$R^8$ represents methyl or trifluoromethyl,
$R^9$ represents chlorine or trifluoromethyl,
Y represents one of the radicals Y1 to Y5 below:

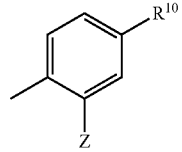

Y1

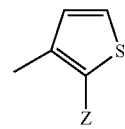

Y2

-continued

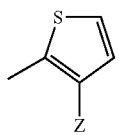
Y3

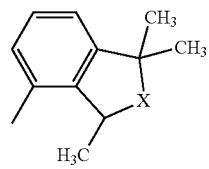
Y4

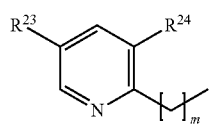
Y5

$R^{10}$ represents hydrogen or fluorine,

X represents —CH$_2$— or O (oxygen),

Z represents one of the radicals Z1, Z2 or Z3 below:

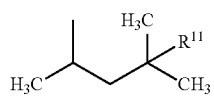
Z1

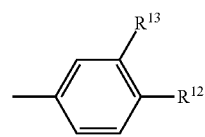
Z2

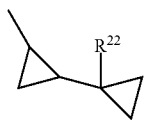
Z3

$R^{11}$ represents hydrogen, fluorine, chlorine, methyl, ethyl, n-, isopropyl, monofluoromethyl, difluoromethyl, trifluoromethyl, monochloromethyl, dichloromethyl or trichloromethyl, $R^{12}$ represents fluorine, chlorine, bromine, methyl, trifluoromethyl, trifluoromethoxy, —CH=N—OCH$_3$ or —C(CH$_3$)=N—OCH$_3$, $R^{13}$ represents hydrogen, fluorine, chlorine, bromine, methyl or trifluoromethyl, m represents an integer from 1 to 4, preferably 2, $R^{22}$ represents hydrogen or C$_{1-4}$-alkyl, preferably hydrogen or methyl, $R^{23}$ and $R^{24}$ represent fluorine, chlorine, bromine difluoromethyl, trifluoromethyl, monochloromethyl, dichloromethyl or trichloromethyl, wherein $R^{23}$ is preferably trifluoromethyl if $R^{24}$ is chlorine.

and (B) an azole of the general formula (II)

$$\text{(II)}$$

in which
Q represents hydrogen or SH,
m represents 0 or 1,
$R^{14}$ represents hydrogen, fluorine, chlorine, phenyl or 4-chlorophenoxy,
$R^{15}$ represents hydrogen or chlorine,
$A^1$ represents a direct bond, —CH$_2$—, —(CH$_2$)$_2$— or —O—,
$A^1$ furthermore represent *—CH$_2$—CHR$^{18}$— or *—CH=CR$^{18}$—, where the bond marked by the * is attached to the phenyl ring, and
$R^{16}$ and $R^{18}$ together represent —CH$_2$—CH$_2$—CH[CH(CH$_3$)$_2$]— or —CH$_2$—CH$_2$—C(CH$_3$)$_2$,
$A^2$ represents C or Si (silicon),
$A^1$ furthermore represents —N(R$^{18}$)— and A$^2$ furthermore together with $R^{16}$ and $R^{17}$ represents the group C=N—R$^6$, in which case $R^{18}$ and $R^{19}$ together represent the group

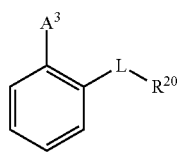

where the bond marked by * is attached to $R^{18}$,
$R^{16}$ represents hydrogen, hydroxyl or cyano,
$R^{17}$ represents 1-cyclopropylethyl, 1-chlorocyclopropyl, C$_1$-C$_4$-alkyl, C$_1$-C$_6$-hydroxyalkyl, C$_1$-C$_4$-alkylcarbonyl, C$_1$-C$_2$-haloalkoxy-C$_1$-C$_2$-alkyl, trimethyl-silyl-C$_1$-C$_2$-alkyl, monofluorophenyl or phenyl,
$R^{16}$ and $R^{17}$ furthermore together represent —O—CH$_2$—CH(R$^{19}$)—O—, —O—CH$_2$—CH(R$^{19}$)—CH$_2$— or —O—CH-(2-chlorophenyl)-,
$R^{19}$ represents hydrogen, C$_1$-C$_4$-alkyl or bromine;

and
(C1) a second azole of the formula (II) (as described above) or
(C2) a strobilurin of the formula (III)

$$\text{(III)}$$

in which

A³ represents one of the groups

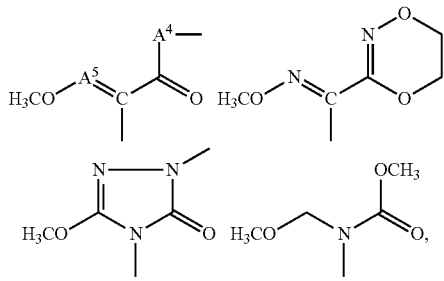

A⁴ represents NH or O,
A⁵ represents N or CH,
L represents one of the groups

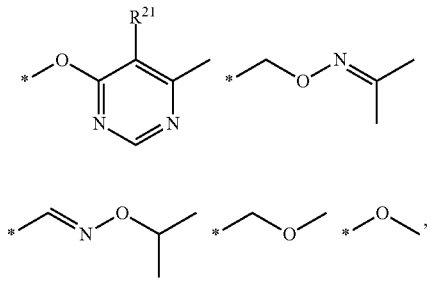

where the bond marked by an asterisk (*) is attached to the phenyl ring,

R²⁰ represents phenyl, phenoxy or pyridinyl, each of which is optionally mono- or disubstituted by identical or different substituents from the group consisting of chlorine, cyano, methyl and trifluoromethyl, or represents 1-(4-chlorophenyl)-pyrazol-3-yl or represents 1,2-propanedione-bis(O-methyloxim)-1-yl, R²¹ represents hydrogen or fluorine.

Surprisingly, the fungicidal activity of the active compound combinations according to the invention is considerably higher than the sum of the activities of the individual active compounds or than the activity of the known mixtures of two components. Thus, an unforeseeable true synergistic effect is present, and not just an addition of activities.

The formula (I) embraces the following preferred mixing partners from the group of the carboxamides:

(I-1)  N-[2-(1,3-dimethylbutyl)phenyl]-1,3-dimethyl-1H-pyrazole-4-carboxamide (known from JP-A 10-251240) of the formula

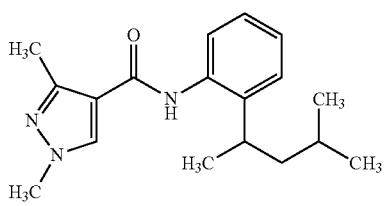 [SMILES: Cc1nn(C)cc1C(=O)Nc1ccccc1C(C)CC(C)C]

(I-2)  N-[2-(1,3-dimethylbutyl)phenyl]-5-fluoro-1,3-dimethyl-1H-pyrazole-4-carboxamide (known from WO 03/010149) of the formula

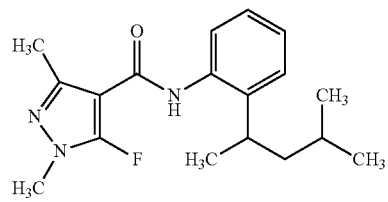 [SMILES: Cc1nn(C)c(F)c1C(=O)Nc1ccccc1C(C)CC(C)C]

(I-3)  N-[2-(1,3-dimethylbutyl)phenyl]-5-chloro-1,3-dimethyl-1H-pyrazole-4-carboxamide (known from JP-A 10-251240) of the formula

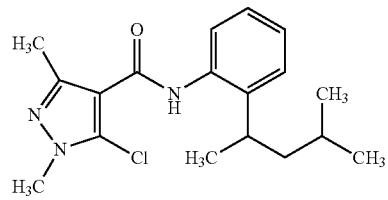 [SMILES: Cc1nn(C)c(Cl)c1C(=O)Nc1ccccc1C(C)CC(C)C]

(I-4)  3-(difluoromethyl)-N-[2-(1,3-dimethylbutyl)phenyl]-1-methyl-1H-pyrazole-4-carboxamide of the formula

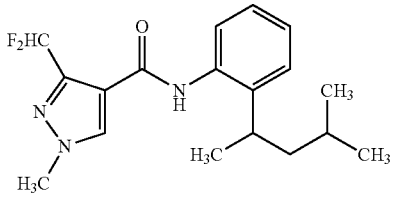 [SMILES: CC(C)CC(C)c1ccccc1NC(=O)c1cn(C)nc1C(F)F]

(I-5)  3-(trifluoromethyl)-N-[2-(1,3-dimethylbutyl)phenyl]-5-fluoro-1-methyl-1H-pyrazole-4-carboxamide (known from WO 2004/067515) of the formula

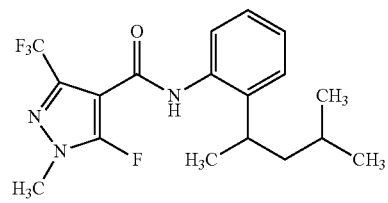 [SMILES: CC(C)CC(C)c1ccccc1NC(=O)c1c(C(F)(F)F)nn(C)c1F]

(I-6)  3-(trifluoromethyl)-N-[2-(1,3-dimethylbutyl)phenyl]-5-chloro-1-methyl-1H-pyrazole-4-carboxamide (known from JP-A 10-251240) of the formula

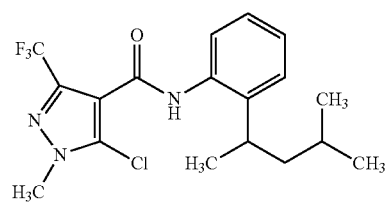

(I-7) 1,3-dimethyl-N-[2-(1,3,3-trimethylbutyl)phenyl]-1H-pyrazole-4-carboxamide of the formula

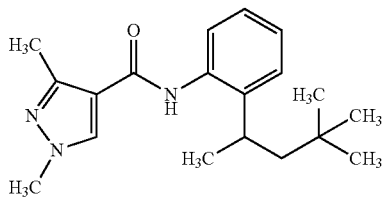 [SMILES: Cc1nn(C)cc1C(=O)Nc1ccccc1C(C)CC(C)(C)C]

(I-8) 5-fluoro-1,3-dimethyl-N-[2-(1,3,3-trimethylbutyl)phenyl]-1H-pyrazole-4-carboxamide (known from WO 03/010149) of the formula

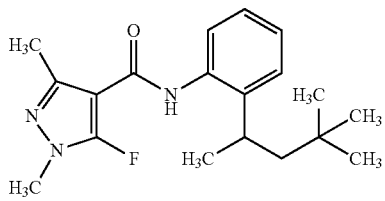 [SMILES: Cc1nn(C)c(F)c1C(=O)Nc1ccccc1C(C)CC(C)(C)C]

(I-9) 3-(difluoromethyl)-1-methyl-N-[2-(1,3,3-trimethylbutyl)phenyl]-1H-pyrazole-4-carboxamide of the formula

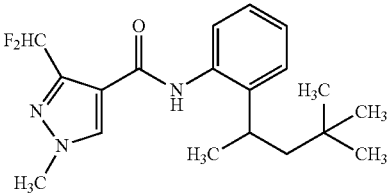 [SMILES: CC(CC(C)(C)C)c1ccccc1NC(=O)c1cn(C)nc1C(F)F]

(I-10) 3-(trifluoromethyl)-1-methyl-N-[2-(1,3,3-trimethylbutyl)phenyl]-1H-pyrazole-4-carboxamide of the formula

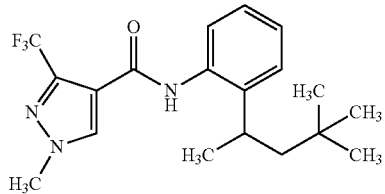 [SMILES: CC(CC(C)(C)C)c1ccccc1NC(=O)c1cn(C)nc1C(F)(F)F]

(I-11) 3-(trifluoromethyl)-5-fluoro-1-methyl-N-[2-(1,3,3-trimethylbutyl)phenyl]-1H-pyrazole-4-carboxamide (known from WO 2004/067515) of the formula

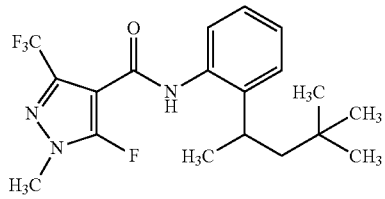

(I-12) 3-(trifluoromethyl)-5-chloro-1-methyl-N-[2-(1,3,3-trimethylbutyl)phenyl]-1H-pyrazole-4-carboxamide of the formula

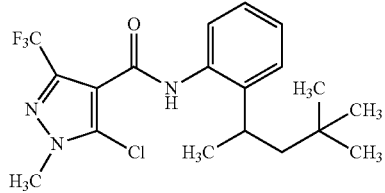 [SMILES: CC(CC(C)(C)C)c1ccccc1NC(=O)c1c(C(F)(F)F)nn(C)c1Cl]

(I-13) N-[2-(1,3-dimethylbutyl)phenyl]-2-iodobenzamide (known from WO 2004/005242) of the formula

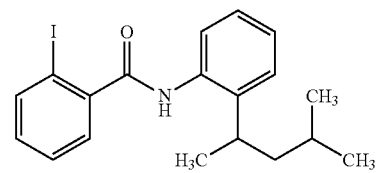 [SMILES: CC(C)CC(C)c1ccccc1NC(=O)c1ccccc1I]

(I-14) 2-iodine-N-[2-(1,3,3-trimethylbutyl)phenyl]benzamide (known from WO 2004/005242) of the formula

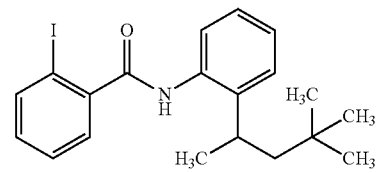 [SMILES: CC(CC(C)(C)C)c1ccccc1NC(=O)c1ccccc1I]

(I-15) N-[2-(1,3-dimethylbutyl)phenyl]-2-(trifluoromethyl)benzamide (known from WO 2004/005242) of the formula

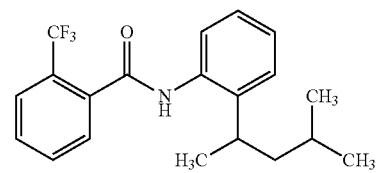 [SMILES: CC(C)CC(C)c1ccccc1NC(=O)c1ccccc1C(F)(F)F]

(I-16) 2-(trifluoromethyl)-N-[2-(1,3,3-trimethylbutyl)phenyl]benzamide (known from WO 2004/005242) of the formula

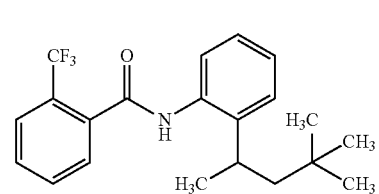 [SMILES: CC(CC(C)(C)C)c1ccccc1NC(=O)c1ccccc1C(F)(F)F]

(I-17) 2-chloro-N-(1,1,3-trimethylindan-4-yl)nicotinamide (known from EP-A 0 256 503) of the formula

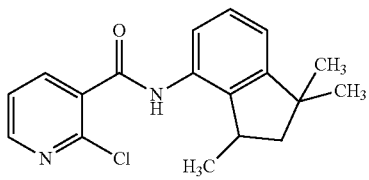 [SMILES: CC1CC(C)(C)c2cccc(NC(=O)c3cccnc3Cl)c21]

(I-18) boscalid (known from DE-A 195 31 813) of the formula

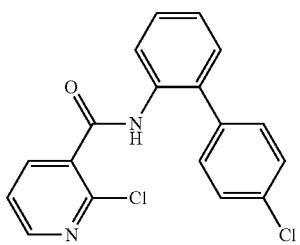 [SMILES: O=C(Nc1ccccc1-c1ccc(Cl)cc1)c1cccnc1Cl]

(I-19) furametpyr (known from EP-A 0 315 502) of the formula

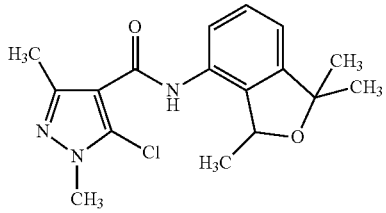

(I-20) N-(3-p-tolylthiophen-2-yl)-1-methyl-3-trifluoromethyl-1H-pyrazole-4-carboxamide (known from EP-A 0 737 682) of the formula

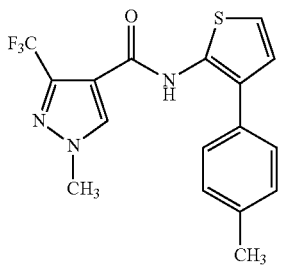 [SMILES: Cc1ccc(-c2ccsc2NC(=O)c2cn(C)nc2C(F)(F)F)cc1]

(I-21) penthiopyrad (known from EP-A 0 737 682) of the formula

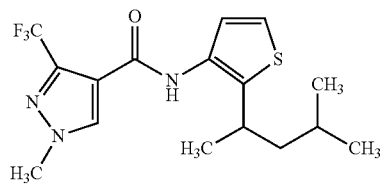 [SMILES: CC(C)CC(C)c1sccc1NC(=O)c1cn(C)nc1C(F)(F)F]

(I-22) N-[2-(1,3-dimethylbutyl)phenyl]-1-methyl-4-(trifluoromethyl)-1H-pyrrole-3-carboxamide (known from WO 02/38542) of the formula

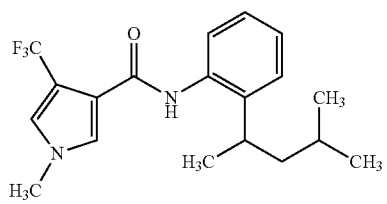 [SMILES: CC(C)CC(C)c1ccccc1NC(=O)c1cn(C)cc1C(F)(F)F]

(I-23) N-(3',4'-dichloro-5-fluoro-1,1'-biphenyl-2-yl)-3-(difluoromethyl)-1-methyl-1H-pyrazole-4-carboxamide (known from WO 03/070705) of the formula

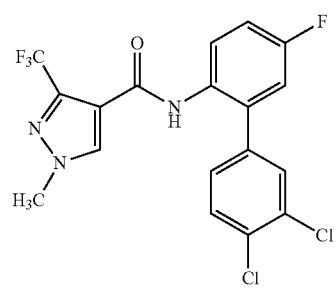 [SMILES: Cn1cc(C(=O)Nc2ccc(F)cc2-c2ccc(Cl)c(Cl)c2)c(C(F)(F)F)n1]

(I-24) 3-(difluoromethyl)-N-{3'-fluoro-4'-[(E)-(methoxyimino)methyl]-1,1'-biphenyl-2-yl}-1-methyl-1H-pyrazole-4-carboxamide (known from WO 02/08197) of the formula

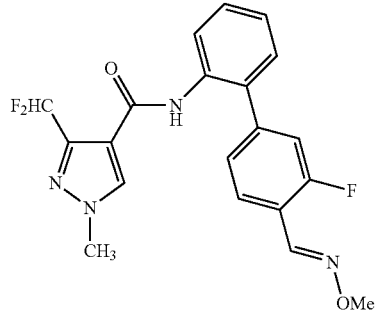 [SMILES: CO/N=C/c1ccc(-c2ccccc2NC(=O)c2cn(C)nc2C(F)F)cc1F]

(I-25) 3-(trifluoromethyl)-N-{3'-fluoro-4'-[(E)-(methoxyimino)methyl]-1,1'-biphenyl-2-yl}-1-methyl-1H-pyrazole-4-carboxamide (known from WO 02/08197) of the formula

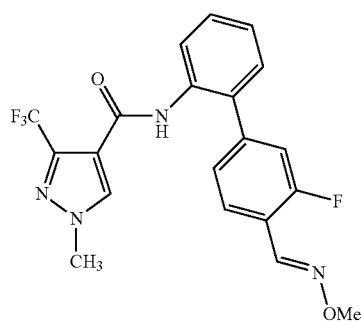 [SMILES: CO/N=C/c1ccc(-c2ccccc2NC(=O)c2cn(C)nc2C(F)(F)F)cc1F]

(I-26) N-(3',4'-dichloro-1,1'-biphenyl-2-yl)-5-fluoro-1,3-dimethyl-1H-pyrazole-4-carboxamide (known from WO 00/14701) of the formula

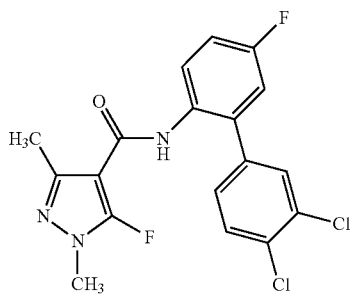 [SMILES: Cc1nn(C)c(F)c1C(=O)Nc1ccc(F)cc1-c1ccc(Cl)c(Cl)c1]

(I-27) N-(4'-chloro-3'-fluoro-1,1'-biphenyl-2-yl)-2-methyl-4-(trifluoromethyl)-1,3-thiazole-5-carboxamide (known from WO 03/066609) of the formula

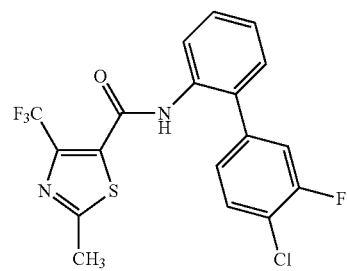 [SMILES: Cc1nc(C(F)(F)F)c(C(=O)Nc2ccccc2-c2ccc(Cl)c(F)c2)s1]

(I-28) N-(4'-chloro-1,1'-biphenyl-2-yl)-4-(difluoromethyl)-2-methyl-1,3-thiazole-5-carboxamide (known from WO 03/066610) of the formula

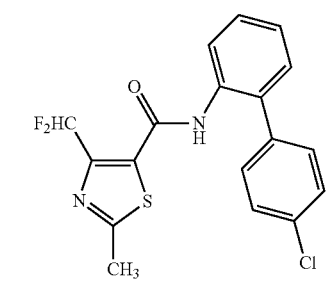 [SMILES: Cc1nc(C(F)F)c(C(=O)Nc2ccccc2-c2ccc(Cl)cc2)s1]

(I-29) N-(4'-bromo-1,1'-biphenyl-2-yl)-4-(difluoromethyl)-2-methyl-1,3-thiazole-5-carboxamide (known from WO 03/066610) of the formula

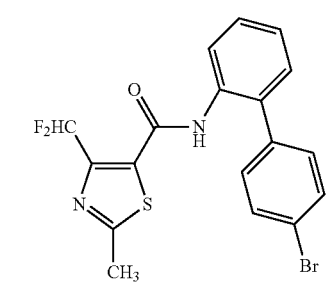 [SMILES: Cc1nc(C(F)F)c(C(=O)Nc2ccccc2-c2ccc(Br)cc2)s1]

(I-30) 4-(difluoromethyl)-2-methyl-N-[4'-(trifluoromethyl)-1,1'-biphenyl-2-yl]-1,3-thiazole-5-carboxamide (known from WO 03/066610) of the formula

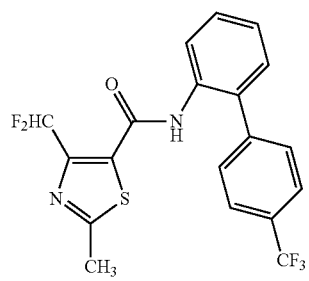

(I-31) N-(4'-iodine-1,1'-biphenyl-2-yl)-4-(difluoromethyl)-2-methyl-1,3-thiazole-5-carboxamide (known from WO 03/066610) of the formula

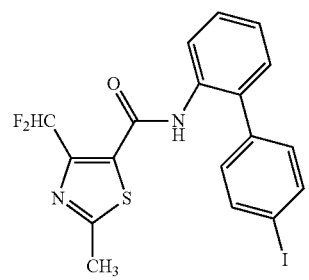 [SMILES: Cc1nc(C(F)F)c(C(=O)Nc2ccccc2-c2ccc(I)cc2)s1]

(I-32) N-(4'-chloro-3'-fluoro-1,1'-biphenyl-2-yl)-2-methyl-4-(difluoromethyl)-1,3-thiazole-5-carboxamide (known from WO 03/066610) of the formula

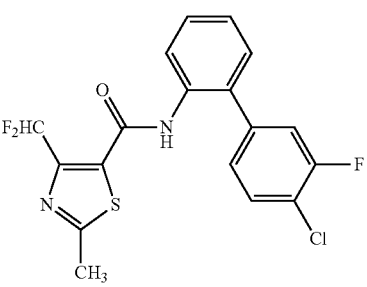 [SMILES: Cc1nc(C(F)F)c(C(=O)Nc2ccccc2-c2ccc(Cl)c(F)c2)s1]

(I-33) (Known from WO 06/015866)

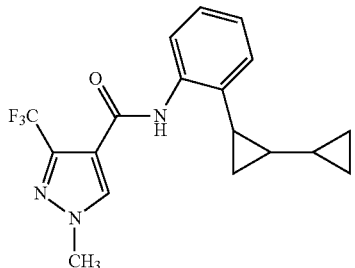

(I-34) (known from WO 04/016088)

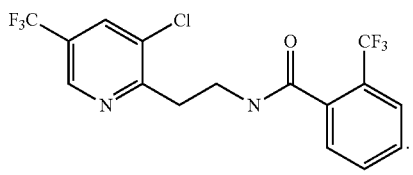 [SMILES: O=C(NCCc1ncc(C(F)(F)F)cc1Cl)c1ccccc1C(F)(F)F]

The formula (I) encompasses the following particularly preferred mixing partners from the group of the carboxamides:

(I-2) N-[2-(1,3-dimethylbutyl)phenyl]-5-fluoro-1,3-dimethyl-1H-pyrazole-4-carboxamide
(I-5) 3-(trifluoromethyl)-N-[2-(1,3-dimethylbutyl)phenyl]-5-fluoro-1-methyl-1H-pyrazole-4-carboxamide
(I-8) 5-fluoro-1,3-dimethyl-N-[2-(1,3,3-trimethylbutyl)phenyl]-1H-pyrazole-4-carboxamide
(I-13) N-[2-(1,3-dimethylbutyl)phenyl]-2-iodobenzamide
(I-15) N-[2-(1,3-dimethylbutyl)phenyl]-2-(trifluoromethyl)benzamide
(I-18) boscalid
(I-19) furametpyr
(I-21) penthiopyrad
(I-22) N-[2-(1,3-dimethylbutyl)phenyl]-1-methyl-4-(trifluoromethyl)-1H-pyrrole-3-carboxamide
(I-23) N-(3',4'-dichloro-5-fluoro-1,1'-biphenyl-2-yl)-3-(difluoromethyl)-1-methyl-1H-pyrazole-4-carboxamide
(I-24) 3-(difluoromethyl)-N-{3'-fluoro-4'-[(E)-(methoxyimino)methyl]-1,1'-biphenyl-2-yl}-1-methyl-1H-pyrazole-4-carboxamide
(I-25) 3-(trifluoromethyl)-N-{3'-fluoro-4'-[(E)-(methoxyimino)methyl]-1,1'-biphenyl-2-yl}-1-methyl-1H-pyrazole-4-carboxamide
(I-26) N-(3',4'-dichloro-1,1'-biphenyl-2-yl)-5-fluoro-1,3-dimethyl-1H-pyrazole-4-carboxamide
(I-29) N-(4'-bromo-1,1'-biphenyl-2-yl)-4-(difluoromethyl)-2-methyl-1,3-thiazole-5-carboxamide
(I-31) N-(4'-iodine-1,1'-biphenyl-2-yl)-4-(difluoromethyl)-2-methyl-1,3-thiazole-5-carboxamide
(I-32) N-(4'-chloro-3'-fluoro-1,1'-biphenyl-2-yl)-2-methyl-4-(difluoromethyl)-1,3-thiazole-5-carboxamide The formula (I) encompasses the following very particularly preferred mixing partners from the group of the carboxamides:

(I-2) N-[2-(1,3-dimethylbutyl)phenyl]-5-fluoro-1,3-dimethyl-1H-pyrazole-4-carboxamide
(I-8) 5-fluoro-1,3-dimethyl-N-[2-(1,3,3-trimethylbutyl)phenyl]-1H-pyrazole-4-carboxamide
(I-13) N-[2-(1,3-dimethylbutyl)phenyl]-2-iodobenzamide
(I-15) N-[2-(1,3-dimethylbutyl)phenyl]-2-(trifluoromethyl)benzamide
(I-18) boscalid
(I-21) penthiopyrad
(I-22) N-[2-(1,3-dimethylbutyl)phenyl]-1-methyl-4-(trifluoromethyl)-1H-pyrrole-3-carboxamide
(I-23) N-(3',4'-dichloro-5-fluoro-1,1'-biphenyl-2-yl)-3-(difluoromethyl)-1-methyl-1H-pyrazole-4-carboxamide
(I-29) N-(4'-bromo-1,1'-biphenyl-2-yl)-4-(difluoromethyl)-2-methyl-1,3-thiazole-5-carboxamide
(I-31) N-(4'-iodine-1,1'-biphenyl-2-yl)-4-(difluoromethyl)-2-methyl-1,3-thiazole-5-carboxamide
(I-32) N-(4'-chloro-3'-fluoro-1,1'-biphenyl-2-yl)-2-methyl-4-(difluoromethyl)-1,3-thiazole-5-carboxamide The formula (II) encompasses the following preferred mixing partners from the group of the azoles:

(II-1) azaconazole (known from DE-A 25 51 560) of the formula

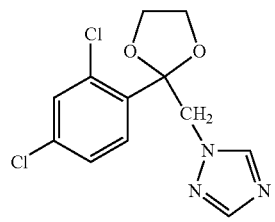 [SMILES: Clc1ccc(C2(Cn3cncn3)OCCO2)c(Cl)c1]

(II-2) etaconazole (known from DE-A 25 51 560) of the formula

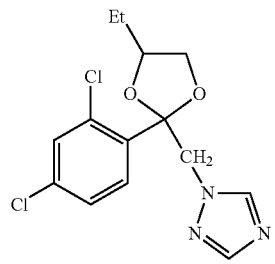 [SMILES: CCC1COC(Cn2cncn2)(c2ccc(Cl)cc2Cl)O1]

(II-3) propiconazole (known from DE-A 25 51 560) of the formula

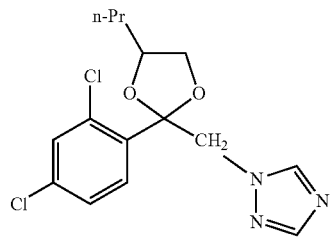

(II-4) difenoconazole (known from EP-A 0 112 284) of the formula

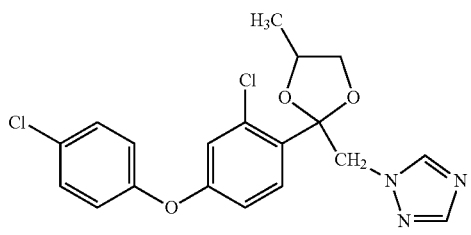 [SMILES: CC1COC(Cn2cncn2)(c2ccc(Oc3ccc(Cl)cc3)cc2Cl)O1]

(II-5) bromuconazole (known from EP-A 0 258 161) of the formula

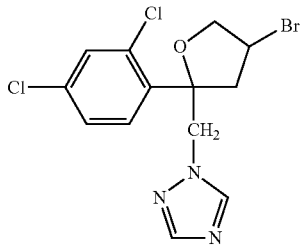 [SMILES: Clc1ccc(C2(Cn3cncn3)CC(Br)CO2)c(Cl)c1]

(II-6) cyproconazole (known from DE-A 34 06 993) of the formula

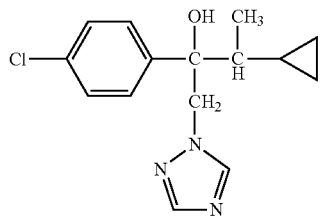 [SMILES: CC(C1CC1)C(O)(Cn1cncn1)c1ccc(Cl)cc1]

(II-7) hexaconazole (known from DE-A 30 42 303) of the formula

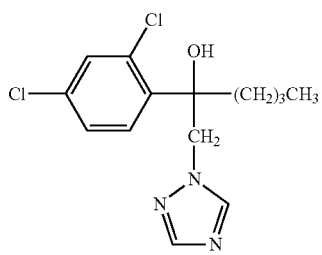

(II-8) penconazole (known from DE-A 27 35 872) of the formula

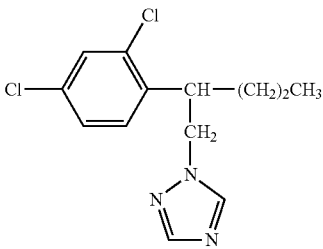

(II-9) myclobutanil (known from EP-A 0 145 294) of the formula

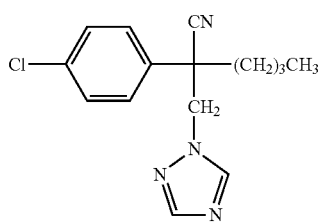

(II-10) tetraconazole (known from EP-A 0 234 242) of the formula

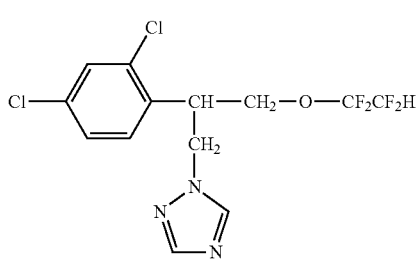

(II-11) flutriafol (known from EP-A 0 015 756) of the formula

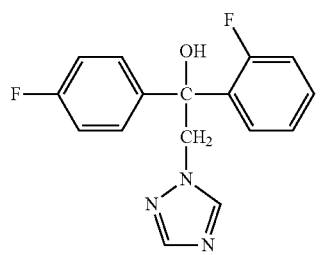 [SMILES: OC(Cn1cncn1)(c1ccc(F)cc1)c1ccccc1F]

(II-12) epoxiconazole (known from EP-A 0 196 038) of the formula

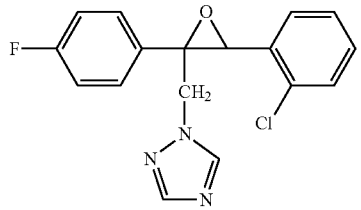 [SMILES: Fc1ccc(C2(Cn3cncn3)OC2c2ccccc2Cl)cc1]

(II-13) flusilazole (known from EP-A 0 068 813) of the formula

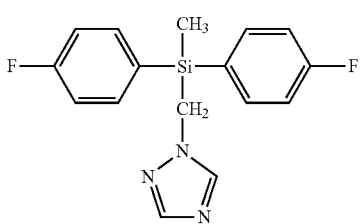 [SMILES: C[Si](Cn1cncn1)(c1ccc(F)cc1)c1ccc(F)cc1]

(II-14) simeconazole (known from EP-A 0 537 957) of the formula

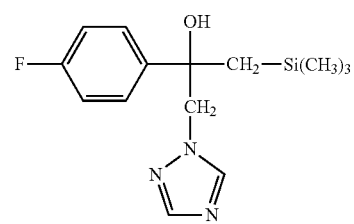

(II-15) prothioconazole (known from WO 96/16048) of the formula

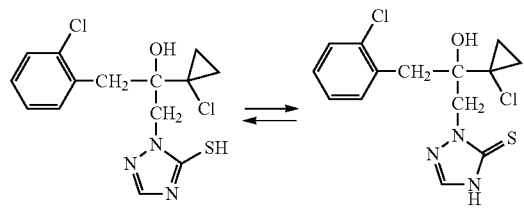 [SMILES: OC(Cc1ccccc1Cl)(Cn1ncnc1S)C1(Cl)CC1 ; OC(Cc1ccccc1Cl)(Cn1nc[nH]c1=S)C1(Cl)CC1]

(II-16) fenbuconazole (known from DE-A 37 21 786) of the formula

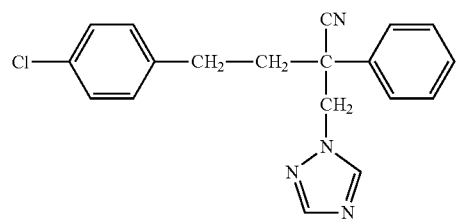 [SMILES: N#CC(CCc1ccc(Cl)cc1)(Cn1cncn1)c1ccccc1]

(II-17) tebuconazole (known from EP-A 0 040 345) of the formula

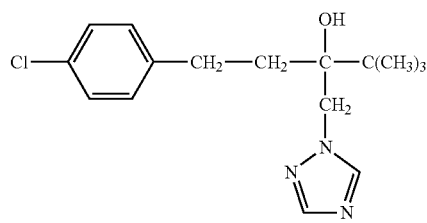 [SMILES: CC(C)(C)C(O)(CCc1ccc(Cl)cc1)Cn1cncn1]

(II-18) ipconazole (known from EP-A 0 329 397) of the formula

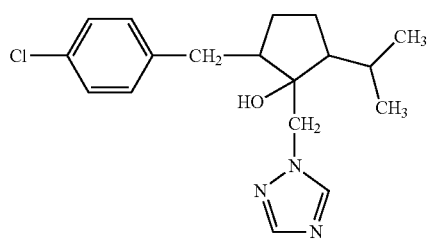 [SMILES: CC(C)C1CCC(Cc2ccc(Cl)cc2)C1(O)Cn1cncn1]

(II-19) metconazole (known from EP-A 0 329 397) of the formula

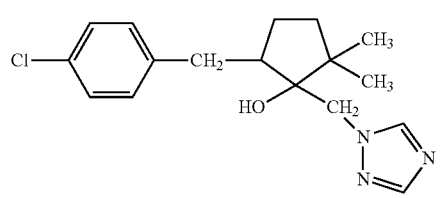 [SMILES: CC1(C)CCC(Cc2ccc(Cl)cc2)C1(O)Cn1cncn1]

(II-20) triticonazole (known from EP-A 0 378 953) of the formula

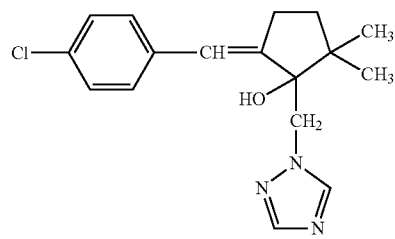 [SMILES: CC1(C)CCC(=Cc2ccc(Cl)cc2)C1(O)Cn1cncn1]

(II-21) bitertanol (known from DE-A 23 24 010) of the formula

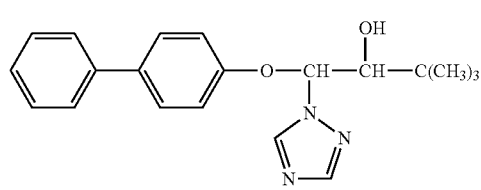 [SMILES: CC(C)(C)C(O)C(Oc1ccc(-c2ccccc2)cc1)n1cncn1]

(II-22) triadimenol (known from DE-A 23 24 010) of the formula

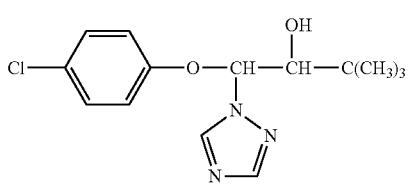 [SMILES: CC(C)(C)C(O)C(Oc1ccc(Cl)cc1)n1cncn1]

(II-23) triadimefon (known from DE-A 22 01 063) of the formula

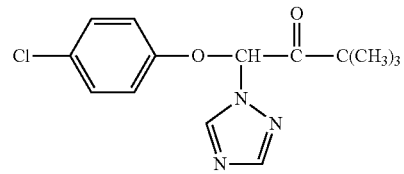 [SMILES: CC(C)(C)C(=O)C(Oc1ccc(Cl)cc1)n1cncn1]

(II-24) fluquinconazole (known from EP-A 0 183 458) of the formula

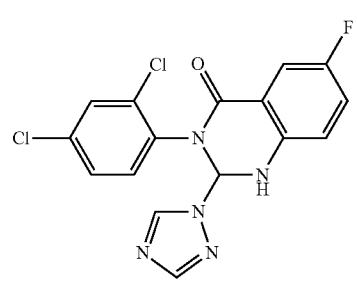 [SMILES: O=C1c2cc(F)ccc2NC(n2cncn2)N1c1ccc(Cl)cc1Cl]

(II-25) quinconazole (known from EP-A 0 183 458) of the formula

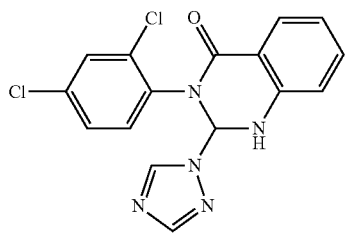 [SMILES: O=C1c2ccccc2NC(n2cncn2)N1c1ccc(Cl)cc1Cl]

The formula (II) encompasses the following particularly preferred mixing partners from the group of the azoles:
(II-3) propiconazole
(II-4) difenoconazole
(II-6) cyproconazole
(II-7) hexaconazole
(II-8) penconazole
(II-9) myclobutanil
(II-10) tetraconazole
(II-11) flutriafol
(II-12) epoxiconazole
(II-13) flusilazole
(II-15) prothioconazole
(II-16) fenbuconazole
(II-17) tebuconazole
(II-19) metconazole
(II-21) bitertanol
(II-22) triadimenol
(II-23) triadimefon
(II-24) fluquinconazole The formula (II) encompasses the following very particularly preferred mixing partners from the group of the azoles:
(II-11) flutriafol
(II-15) prothioconazole
(II-17) tebuconazole
(II-21) bitertanol
(II-22) triadimenol
(II-24) fluquinconazole The formula (II) encompasses the following especially preferred mixing partners from the group of the azoles:
(II-11) flutriafol
(II-15) prothioconazole
(II-17) tebuconazole
(II-24) fluquinconazole The formula (III) encompasses the following preferred mixing partners from the group of the strobilurins:
(III-1) azoxystrobin (known from EP-A 0 382 375) of the formula

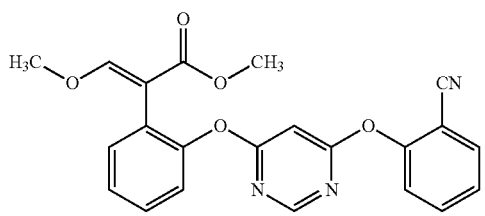 [SMILES: CO/C=C(/C(=O)OC)c1ccccc1Oc1cc(Oc2ccccc2C#N)ncn1]

(III-2) fluoxastrobin (known from DE-A 196 02 095) of the formula

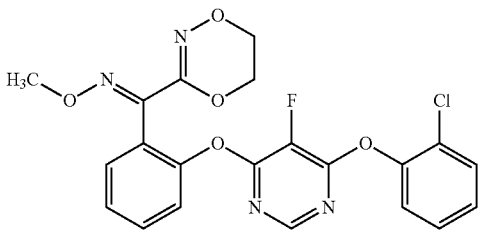 [SMILES: CO/N=C(/C1=NOCCO1)c1ccccc1Oc1ncnc(Oc2ccccc2Cl)c1F]

(III-3) (2E)-2-(2-{[6-(3-chloro-2-methylphenoxy)-5-fluoro-4-pyrimidinyl]oxy}phenyl)-2-(methoxyimino)-N-methylethanamide (known from DE-A 196 46 407, EP-B 0 712 396) of the formula

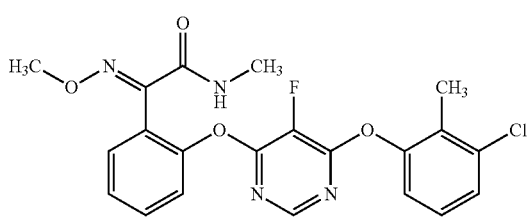 [SMILES: CNC(=O)/C(=N/OC)c1ccccc1Oc1ncnc(Oc2cccc(Cl)c2C)c1F]

(III-4) trifloxystrobin (known from EP-A 0 460 575) of the formula

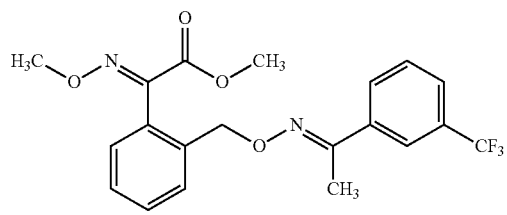 [SMILES: CO/N=C(/C(=O)OC)c1ccccc1CO/N=C(\C)c1cccc(C(F)(F)F)c1]

(III-5) (2E)-2-(methoxyimino)-N-methyl-2-(2-{[({(1E)-1-[3-(trifluoromethyl)phenyl]ethylidene}amino)oxy]methyl}phenyl)ethanamide (known from EP-A 0 569 384) of the formula

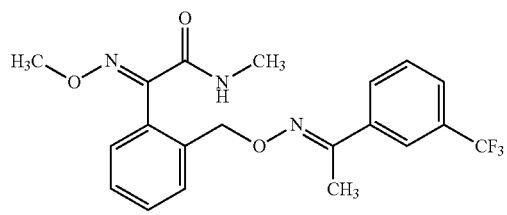 [SMILES: CNC(=O)/C(=N/OC)c1ccccc1CO/N=C(\C)c1cccc(C(F)(F)F)c1]

(III-6) (2E)-2-(methoxyimino)-N-methyl-2-{2-[(E)-({1-[3-(trifluoromethyl)phenyl]ethoxy}imino)methyl]phenyl}ethanamide (known from EP-A 0 596 254) of the formula

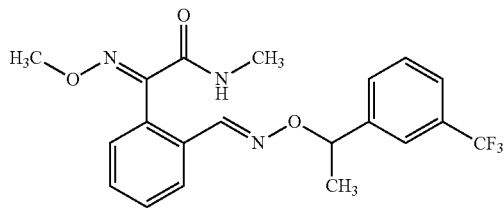 [SMILES: CNC(=O)/C(=N/OC)c1ccccc1/C=N/OC(C)c1cccc(C(F)(F)F)c1]

(III-7) orysastrobin (known from DE-A 195 39 324) of the formula

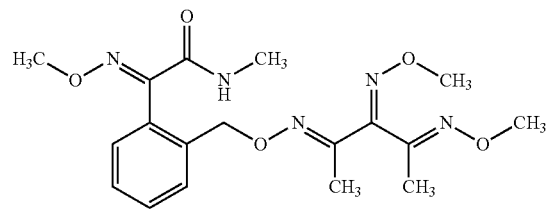

(III-8) 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one (known from WO 98/23155) of the formula

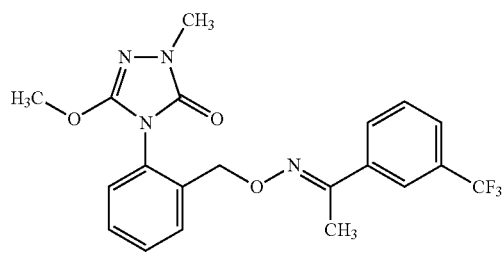 [SMILES: COc1nn(C)c(=O)n1-c1ccccc1CO/N=C(\C)c1cccc(C(F)(F)F)c1]

(III-9) kresoxim-methyl (known from EP-A 0 253 213) of the formula

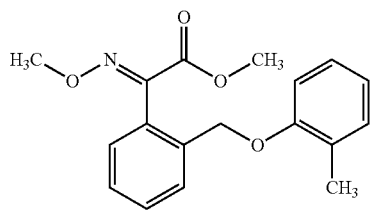 [SMILES: CO/N=C(/C(=O)OC)c1ccccc1COc1ccccc1C]

(III-10) dimoxystrobin (known from EP-A 0 398 692) of the formula

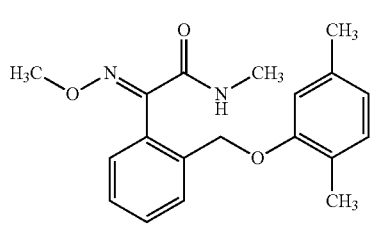 [SMILES: CNC(=O)/C(=N/OC)c1ccccc1COc1cc(C)ccc1C]

(III-11) picoxystrobin (known from EP-A 0 278 595) of the formula

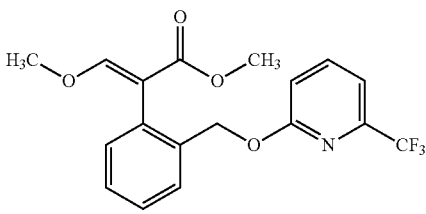 [SMILES: CO/C=C(/C(=O)OC)c1ccccc1COc1cccc(C(F)(F)F)n1]

(III-12) pyraclostrobin (known from DE-A 44 23 612) of the formula

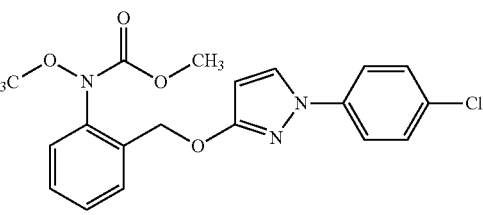

(III-13) metominostrobin (known from EP-A 0 398 692) of the formula

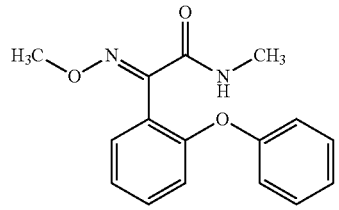 [SMILES: CNC(=O)/C(=N/OC)c1ccccc1Oc1ccccc1]

The formula (III) encompasses the following particularly preferred mixing partners from the group of the strobilurins:
(III-1) azoxystrobin
(III-2) fluoxastrobin
(III-3) (2E)-2-(2-{[6-(3-chloro-2-methylphenoxy)-5-fluoro-4-pyrimidinyl]oxy}phenyl)-2-(methoxyimino)-N-methylethanamide
(III-4) trifloxystrobin
(III-5) (2E)-2-(methoxyimino)-N-methyl-2-(2-{[({(1E)-1-[3-(trifluoromethyl)phenyl]ethylidene}amino)oxy]methyl}phenyl)ethanamide
(III-6) (2E)-2-(methoxyimino)-N-methyl-2-{2-[(E)-({1-[3-(trifluoromethyl)phenyl]ethoxy}imino)methyl]phenyl}ethanamide
(III-8) 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one
(III-9) kresoxim-methyl
(III-11) picoxystrobin
(III-12) pyraclostrobin The formula (III) encompasses the following very particularly preferred mixing partners from the group of the strobilurins:
(III-1) azoxystrobin
(III-2) fluoxastrobin
(III-3) (2E)-2-(2-{[6-(3-chloro-2-methylphenoxy)-5-fluoro-4-pyrimidinyl]oxy}phenyl)-2-(methoxyimino)-N-methylethanamide (III-4) trifloxystrobin
(III-12) pyraclostrobin Active compound combinations which are emphasized and which in each case comprise an active compound from the groups (A), (B) and (C1) or (C2) mentioned above are listed below.

These active compound combinations, which are emphasized, comprise in each case one active compound from group (A) selected from the following compounds:
- (I-2) N-[2-(1,3-dimethylbutyl)phenyl]-5-fluoro-1,3-dimethyl-1H-pyrazole-4-carboxamide
- (I-8) 5-fluoro-1,3-dimethyl-N-[2-(1,3,3-trimethylbutyl)phenyl]-1H-pyrazole-4-carboxamide
- (I-13) N-[2-(1,3-dimethylbutyl)phenyl]-2-iodobenzamide
- (I-15) N-[2-(1,3-dimethylbutyl)phenyl]-2-(trifluoromethyl)benzamide
- (I-18) boscalid
- (I-21) penthiopyrad
- (I-22) N-[2-(1,3-dimethylbutyl)phenyl]-1-methyl-4-(trifluoromethyl)-1H-pyrrole-3-carboxamide
- (I-23) N-(3',4'-dichloro-5-fluoro-1,1'-biphenyl-2-yl)-3-(difluoromethyl)-1-methyl-1H-pyrazole-4-carboxamide
- (I-29) N-(4'-bromo-1,1'-biphenyl-2-yl)-4-(difluoromethyl)-2-methyl-1,3-thiazole-5-carboxamide
- (I-31) N-(4'-iodine-1,1'-biphenyl-2-yl)-4-(difluoromethyl)-2-methyl-1,3-thiazole-5-carboxamide
- (I-32) N-(4'-chloro-3'-fluoro-1,1'-biphenyl-2-yl)-2-methyl-4-(difluoromethyl)-1,3-thiazole-5-carboxamide and also two further active compounds from groups (B) and (C1) or (C2), as combined in Table 1:

TABLE 1

| No. | Active compound (B) | Active compound (C1)/(C2) |
| --- | --- | --- |
| 1.1 | (II-11) flutriafol | (II-15) prothioconazole |
| 1.2 | (II-11) flutriafol | (II-17) tebuconazole |
| 1.3 | (II-11) flutriafol | (II-21) bitertanol |
| 1.4 | (II-11) flutriafol | (II-22) triadimenol |
| 1.5 | (II-11) flutriafol | (II-24) fluquinconazole |
| 1.6 | (II-11) flutriafol | (III-1) azoxystrobin |
| 1.7 | (II-11) flutriafol | (III-2) fluoxastrobin |
| 1.8 | (II-11) flutriafol | (III-3) (2E)-2-(2-{[6-(3-chloro-2-methylphenoxy)-5-fluoro-4-pyrimidinyl]oxy}phenyl)-2-(methoxyimino)-N-methylethanamide |
| 1.9 | (II-11) flutriafol | (III-4) trifloxystrobin |
| 1.10 | (II-11) flutriafol | (III-12) pyraclostrobin |
| 1.11 | (II-15) prothioconazole | (II-17) tebuconazole |
| 1.12 | (II-15) prothioconazole | (II-21) bitertanol |
| 1.13 | (II-15) prothioconazole | (II-22) triadimenol |
| 1.14 | (II-15) prothioconazole | (II-24) fluquinconazole |
| 1.15 | (II-15) prothioconazole | (III-1) azoxystrobin |
| 1.16 | (II-15) prothioconazole | (III-2) fluoxastrobin |
| 1.17 | (II-15) prothioconazole | (III-3) (2E)-2-(2-{[6-(3-chloro-2-methylphenoxy)-5-fluoro-4-pyrimidinyl]oxy}phenyl)-2-(methoxyimino)-N-methylethanamide |
| 1.18 | (II-15) prothioconazole | (III-4) trifloxystrobin |
| 1.19 | (II-15) prothioconazole | (III-12) pyraclostrobin |
| 1.20 | (II-17) tebuconazole | (II-21) bitertanol |
| 1.21 | (II-17) tebuconazole | (II-22) triadimenol |
| 1.22 | (II-17) tebuconazole | (II-24) fluquinconazole |
| 1.23 | (II-17) tebuconazole | (III-1) azoxystrobin |
| 1.24 | (II-17) tebuconazole | (III-2) fluoxastrobin |
| 1.25 | (II-17) tebuconazole | (III-3) (2E)-2-(2-{[6-(3-chloro-2-methylphenoxy)-5-fluoro-4-pyrimidinyl]oxy}phenyl)-2-(methoxyimino)-N-methylethanamide |
| 1.26 | (II-17) tebuconazole | (III-4) trifloxystrobin |
| 1.27 | (II-17) tebuconazole | (III-12) pyraclostrobin |
| 1.28 | (II-21) bitertanol | (II-22) triadimenol |
| 1.29 | (II-21) bitertanol | (II-24) fluquinconazole |
| 1.30 | (II-21) bitertanol | (III-1) azoxystrobin |
| 1.31 | (II-21) bitertanol | (III-2) fluoxastrobin |
| 1.32 | (II-21) bitertanol | (III-3) (2E)-2-(2-{[6-(3-chloro-2-methylphenoxy)-5-fluoro-4-pyrimidinyl]oxy}phenyl)-2-(methoxyimino)-N-methylethanamide |
| 1.33 | (II-21) bitertanol | (III-4) trifloxystrobin |
| 1.34 | (II-21) bitertanol | (III-12) pyraclostrobin |
| 1.35 | (II-22) triadimenol | (II-24) fluquinconazole |
| 1.36 | (II-22) triadimenol | (III-1) azoxystrobin |
| 1.37 | (II-22) triadimenol | (III-2) fluoxastrobin |
| 1.38 | (II-22) triadimenol | (III-3) (2E)-2-(2-{[6-(3-chloro-2-methylphenoxy)-5-fluoro-4-pyrimidinyl]oxy}phenyl)-2-(methoxyimino)-N-methylethanamide |
| 1.39 | (II-22) triadimenol | (III-4) trifloxystrobin |
| 1.40 | (II-22) triadimenol | (III-12) pyraclostrobin |
| 1.41 | (II-24) fluquinconazole | (III-1) azoxystrobin |
| 1.42 | (II-24) fluquinconazole | (III-2) fluoxastrobin |
| 1.43 | (II-24) fluquinconazole | (III-3) (2E)-2-(2-{[6-(3-chloro-2-methylphenoxy)-5-fluoro-4-pyrimidinyl]oxy}phenyl)-2-(methoxyimino)-N-methylethanamide |
| 1.44 | (II-24) fluquinconazole | (III-4) trifloxystrobin |
| 1.45 | (II-24) fluquinconazole | (III-12) pyraclostrobin |

From among these active compound combinations, even more emphasis is given to the following combinations listed in Table 2.

TABLE 2

| No. | Active compound (A) | Active compound (B) | Active compound (C1)/(C2) |
| --- | --- | --- | --- |
| 2.1 | (I-2) N-[2-(1,3-dimethylbutyl)phenyl]-5-fluoro-1,3-dimethyl-1H-pyrazole-4-carboxamide | (II-24) fluquinconazole | (III-2) fluoxastrobin |
| 2.2 | (I-2) N-[2-(1,3-dimethylbutyl)phenyl]-5-fluoro-1,3-dimethyl-1H-pyrazole-4-carboxamide | (II-22) triadimenol | (III-2) fluoxastrobin |
| 2.3 | (I-2) N-[2-(1,3-dimethylbutyl)phenyl]-5-fluoro-1,3-dimethyl-1H-pyrazole-4-carboxamide | (II-24) fluquinconazole | (II-22) triadimenol |
| 2.4 | (I-2) N-[2-(1,3-dimethylbutyl)phenyl]-5-fluoro-1,3-dimethyl-1H-pyrazole-4-carboxamide | (II-18) ipconazole | (III-4) trifloxystrobin |
| 2.5 | (I-2) N-[2-(1,3-dimethylbutyl)phenyl]-5-fluoro-1,3-dimethyl-1H-pyrazole-4-carboxamide | (II-11) flutriafol | (II-15) prothioconazole |

TABLE 2-continued

| No. | Active compound (A) | Active compound (B) | Active compound (C1)/(C2) |
|---|---|---|---|
| 2.6 | (I-2) N-[2-(1,3-dimethylbutyl)phenyl]-5-fluoro-1,3-dimethyl-1H-pyrazole-4-carboxamide | (II-11) flutriafol | (II-17) tebuconazole |
| 2.7 | (I-2) N-[2-(1,3-dimethylbutyl)phenyl]-5-fluoro-1,3-dimethyl-1H-pyrazole-4-carboxamide | (II-11) flutriafol | (III-2) fluoxastrobin |
| 2.8 | (I-2) N-[2-(1,3-dimethylbutyl)phenyl]-5-fluoro-1,3-dimethyl-1H-pyrazole-4-carboxamide | (II-11) flutriafol | (III-4) trifloxystrobin |
| 2.9 | (I-2) N-[2-(1,3-dimethylbutyl)phenyl]-5-fluoro-1,3-dimethyl-1H-pyrazole-4-carboxamide | (II-15) prothioconazole | (II-17) tebuconazole |
| 2.10 | (I-2) N-[2-(1,3-dimethylbutyl)phenyl]-5-fluoro-1,3-dimethyl-1H-pyrazole-4-carboxamide | (II-15) prothioconazole | (III-2) fluoxastrobin |
| 2.11 | (I-2) N-[2-(1,3-dimethylbutyl)phenyl]-5-fluoro-1,3-dimethyl-1H-pyrazole-4-carboxamide | (II-15) prothioconazole | (III-4) trifloxystrobin |
| 2.12 | (I-2) N-[2-(1,3-dimethylbutyl)phenyl]-5-fluoro-1,3-dimethyl-1H-pyrazole-4-carboxamide | (II-17) tebuconazole | (III-2) fluoxastrobin |
| 2.13 | (I-2) N-[2-(1,3-dimethylbutyl)phenyl]-5-fluoro-1,3-dimethyl-1H-pyrazole-4-carboxamide | (II-17) tebuconazole | (III-4) trifloxystrobin |
| 2.14 | (I-18) boscalid | (II-11) flutriafol | (II-15) prothioconazole |
| 2.15 | (I-18) boscalid | (II-11) flutriafol | (II-17) tebuconazole |
| 2.16 | (I-18) boscalid | (II-11) flutriafol | (III-2) fluoxastrobin |
| 2.17 | (I-18) boscalid | (II-11) flutriafol | (III-4) trifloxystrobin |
| 2.18 | (I-18) boscalid | (II-15) prothioconazole | (II-17) tebuconazole |
| 2.19 | (I-18) boscalid | (II-15) prothioconazole | (III-2) fluoxastrobin |
| 2.20 | (I-18) boscalid | (II-15) prothioconazole | (III-4) trifloxystrobin |
| 2.21 | (I-18) boscalid | (II-17) tebuconazole | (III-2) fluoxastrobin |
| 2.22 | (I-18) boscalid | (II-17) tebuconazole | (III-4) trifloxystrobin |
| 2.23 | (I-21) penthiopyrad | (II-11) flutriafol | (II-15) prothioconazole |
| 2.24 | (I-21) penthiopyrad | (II-11) flutriafol | (II-17) tebuconazole |
| 2.25 | (I-21) penthiopyrad | (II-11) flutriafol | (III-2) fluoxastrobin |
| 2.26 | (I-21) penthiopyrad | (II-11) flutriafol | (III-4) trifloxystrobin |
| 2.27 | (I-21) penthiopyrad | (II-15) prothioconazole | (II-17) tebuconazole |
| 2.28 | (I-21) penthiopyrad | (II-15) prothioconazole | (III-2) fluoxastrobin |
| 2.29 | (I-21) penthiopyrad | (II-15) prothioconazole | (III-4) trifloxystrobin |
| 2.30 | (I-21) penthiopyrad | (II-17) tebuconazole | (III-2) fluoxastrobin |
| 2.31 | (I-21) penthiopyrad | (II-17) tebuconazole | (III-4) trifloxystrobin |
| 2.32 | (I-23) N-(3',4'-dichloro-5-fluoro-1,1'-biphenyl-2-yl)-3-(difluoromethyl)-1-methyl-1H-pyrazole-4-carboxamide | (II-11) flutriafol | (II-15) prothioconazole |
| 2.33 | (I-23) N-(3',4'-dichloro-5-fluoro-1,1'-biphenyl-2-yl)-3-(difluoromethyl)-1-methyl-1H-pyrazole-4-carboxamide | (II-11) flutriafol | (II-17) tebuconazole |
| 2.34 | (I-23) N-(3',4'-dichloro-5-fluoro-1,1'-biphenyl-2-yl)-3-(difluoromethyl)-1-methyl-1H-pyrazole-4-carboxamide | (II-11) flutriafol | (III-2) fluoxastrobin |
| 2.35 | (I-23) N-(3',4'-dichloro-5-fluoro-1,1'-biphenyl-2-yl)-3-(difluoromethyl)-1-methyl-1H-pyrazole-4-carboxamide | (II-11) flutriafol | (III-4) trifloxystrobin |
| 2.36 | (I-23) N-(3',4'-dichloro-5-fluoro-1,1'-biphenyl-2-yl)-3-(difluoromethyl)-1-methyl-1H-pyrazole-4-carboxamide | (II-15) prothioconazole | (II-17) tebuconazole |
| 2.37 | (I-23) N-(3',4'-dichloro-5-fluoro-1,1'-biphenyl-2-yl)-3-(difluoromethyl)-1-methyl-1H-pyrazole-4-carboxamide | (II-15) prothioconazole | (III-2) fluoxastrobin |
| 2.38 | (I-23) N-(3',4'-dichloro-5-fluoro-1,1'-biphenyl-2-yl)-3-(difluoromethyl)-1-methyl-1H-pyrazole-4-carboxamide | (II-15) prothioconazole | (III-4) trifloxystrobin |

TABLE 2-continued

| No. | Active compound (A) | Active compound (B) | Active compound (C1)/(C2) |
|---|---|---|---|
| 2.39 | (I-23) N-(3',4'-dichloro-5-fluoro-1,1'-biphenyl-2-yl)-3-(difluoromethyl)-1-methyl-1H-pyrazole-4-carboxamide | (II-17) tebuconazole | (III-2) fluoxastrobin |
| 2.40 | (I-23) N-(3',4'-dichloro-5-fluoro-1,1'-biphenyl-2-yl)-3-(difluoromethyl)-1-methyl-1H-pyrazole-4-carboxamide | (II-17) tebuconazole | (III-4) trifloxystrobin |

In addition to the active compound (A) of the formula (I), the active compound combinations according to the invention comprise an active compound (B) of the formula (II) and an active compound (C1) of the formula (II) or an active compound (C2) of the formula (III). In addition, they may also comprise further added, fungicidally active components.

If the active compounds in the active compound combinations according to the invention are present in certain weight ratios, the synergistic effect is particularly pronounced. However, the weight ratios of the active compounds in the active compound combinations can be varied within a relatively wide range. In general, from 0.05 to 20 parts by weight, preferably from 0.1 to 10 parts by weight, of active compound (B) of the formula (II) and from 0.02 to 50 parts by weight, preferably from 0.05 to 20 parts by weight, particularly preferably from 0.1 to 10 parts by weight, of active compound (C) of the formula (III) are present per part by weight of active compound (A) of the formula (I). The mixing ratio is preferably to be chosen such that a synergistic mixture is obtained.

The active compound combinations according to the invention have very good fungicidal properties and can be used for controlling phytopathogenic fungi, such as Plasmodiophoromycetes, Oomycetes, Chytridiomycetes, Zygomycetes, Ascomycetes, Basidiomycetes, Deuteromycetes etc.

The active compound combinations according to the invention are particularly suitable for controlling *Mycosphaerella graminicola* (=*Septoria tritici*), *Puccinia recondita*, *Erysiphe graminis* and *Phakopsora pachyrhizi*.

Some pathogens causing fungal diseases which come under the generic names listed above may be mentioned as examples, but not by way of limitation:
diseases caused by powdery mildew pathogens, such as, for example,
*Blumeria* species, such as, for example, *Blumeria graminis*;
*Podosphaera* species, such as, for example, *Podosphaera leucotricha*;
*Sphaerotheca* species, such as, for example, *Sphaerotheca fuliginea*;
*Uncinula* species, such as, for example, *Uncinula necator*;
diseases caused by rust disease pathogens, such as, for example,
*Gymnosporangium* species, such as, for example, *Gymnosporangium sabinae*;
*Hemileia* species, such as, for example, *Hemileia vastatrix*;
*Phakopsora* species, such as, for example, *Phakopsora pachyrhizi* and *Phakopsora meibomiae*;
*Puccinia* species, such as, for example, *Puccinia recondita*;
*Uromyces* species, such as, for example, *Uromyces appendiculatus*;
diseases caused by pathogens from the group of the Oomycetes, such as, for example,
*Bremia* species, such as, for example, *Bremia lactucae*;
*Peronospora* species, such as, for example, *Peronospora pisi* or *P. brassicae*;
*Phytophthora* species, such as, for example *Phytophthora infestans*;
*Plasmopara* species, such as, for example, *Plasmopara viticola*;
*Pseudoperonospora* species, such as, for example, *Pseudoperonospora humuli* or *Pseudoperonospora cubeusis*;
*Pythium* species, such as, for example, *Pythium ultimum*;
leaf blotch diseases and leaf wilt diseases caused, for example, by
*Alternaria* species, such as, for example, *Alternaria solani*;
*Cercospora* species, such as, for example, *Cercospora beticola*;
*Cladiosporium* species, such as, for example, *Cladiosporium cucumerinum*;
*Cochliobolus* species, such as, for example, *Cochliobolus sativus* (conidia form: *Drechslera*, Syn: *Helminthosporium*);
*Colletotrichum* species, such as, for example, *Colletotrichum lindemuthanium*;
*Cycloconium* species, such as, for example, *Cycloconium oleaginum*;
*Diaporthe* species, such as, for example, *Diaporthe citri*;
*Elsinoe* species, such as, for example, *Elsinoe fawcettii*;
*Gloeosporium* species, such as, for example, *Gloeosporium laeticolor*;
*Glomerella* species, such as, for example, *Glomerella cingulata*;
*Guignardia* species, such as, for example, *Guignardia bidwelli*;
*Leptosphaeria* species, such as, for example, *Leptosphaeria maculans*;
*Magnaporthe* species, such as, for example, *Magnaporthe grisea*;
*Mycosphaerella* species, such as, for example, *Mycosphaerella graminicola*;
*Phaeosphaeria* species, such as, for example, *Phaeosphaeria nodorum*;
*Pyrenophora* species, such as, for example, *Pyrenophora teres*;
*Ramularia* species, such as, for example, *Ramularia collocygni*;
*Rhynchosporium* species, such as, for example, *Rhynchosporium secalis*;
*Septoria* species, such as, for example, *Septoria apii*;
*Typhula* species, such as, for example, *Typhula incarnata*;
*Venturia* species, such as, for example, *Venturia inaequalis*;
root and stem diseases caused, for example, by
*Corticium* species, such as, for example, *Corticium graminearum*;
*Fusarium* species, such as, for example, *Fusarium oxysporum*;
*Gaeumannomyces* species, such as, for example, *Gaeumannomyces graminis*;
*Rhizoctonia* species, such as, for example, *Rhizoctonia solani*;
*Tapesia* species, such as, for example, *Tapesia acuformis*;

*Thielaviopsis* species, such as, for example, *Thielaviopsis basicola*;

ear and panicle diseases (including maize cobs) caused, for example, by

*Alternaria* species, such as, for example, *Alternaria* spp.;
*Aspergillus* species, such as, for example, *Aspergillus flavus*;
*Cladosporium* species, such as, for example, *Cladosporium* spp.;
*Claviceps* species, such as, for example, *Claviceps purpurea*;
*Fusarium* species, such as, for example, *Fusarium culmorum*;
*Gibberella* species, such as, for example, *Gibberella zeae*;
*Monographella* species, such as, for example, *Monographella nivalis*;

diseases caused by smut fungi, such as, for example,
*Sphacelotheca* species, such as, for example, *Sphacelotheca reiliana*;
*Tilletia* species, such as, for example, *Tilletia caries*;
*Urocystis* species, such as, for example, *Urocystis occulta*;
*Ustilago* species, such as, for example, *Ustilago nuda*;

fruit rot caused, for example, by

*Aspergillus* species, such as, for example, *Aspergillus flavus*;
*Botrytis* species, such as, for example, *Botrytis cinerea*;
*Penicillium* species, such as, for example, *Penicillium expansum*;
*Sclerotinia* species, such as, for example, *Sclerotinia sclerotiorum*;
*Verticilium* species, such as, for example, *Verticilium alboatrum*;

seed- and soil-borne rot and wilt diseases, and also diseases of seedlings, caused, for example, by

*Fusarium* species, such as, for example, *Fusarium culmorum*;
*Phytophthora* species, such as, for example, *Phytophthora cactorum*;
*Pythium* species, such as, for example, *Pythium ultimum*;
*Rhizoctonia* species, such as, for example, *Rhizoctonia solani*;
*Sclerotium* species, such as, for example, *Sclerotium rolfsii*;

cancerous diseases, galls and witche's broom caused, for example, by

*Nectria* species, such as, for example, *Nectria galligena*;

wilt diseases caused, for example, by

*Monilinia* species, such as, for example, *Monilinia laxa*;

deformations of leaves, flowers and fruits caused, for example, by

*Taphrina* species, such as, for example, *Taphrina deformans*;

degenerative diseases of woody plants caused, for example, by

*Esca* species, such as, for example, *Phaemoniella clamydospora*;

diseases of flowers and seeds caused, for example, by

*Botrytis* species, such as, for example, *Botrytis cinerea*;

diseases of plant tubers caused, for example, by

*Rhizoctonia* species, such as, for example, *Rhizoctonia solani*;

diseases cause by bacterial pathogens, such as, for example,

*Xanthomonas* species, such as, for example, *Xanthomonas campestris* pv. *oryzae*;
*Pseudomonas* species, such as, for example, *Pseudomonas syringae* pv. *lachrymans*;
*Erwinia* species, such as, for example, *Erwinia amylovora*.

With preference, it is possible to control the following diseases of soya beans: fungal diseases on leaves, stems, pods and seeds, caused, for example, by alternaria leaf spot (*Alternaria* spec. *atrans tenuissima*), anthracnose (*Colletotrichum gloeosporoides dematium* var. *truncatum*), brown spot (*Septoria glycines*), cercospora leaf spot and blight (*Cercospora kikuchii*), choanephora leaf blight (*Choanephora infundibulifera trispora* (Syn.)), dactuliophora leaf spot (*Dactuliophora glycines*), downy mildew (*Peronospora manshurica*), drechslera blight (*Drechslera glycini*), frogeye leaf spot (*Cercospora sojina*), leptosphaerulina leaf spot (*Leptosphaerulina trifolii*), phyllostica leaf spot (*Phyllosticta sojaecola*), powdery mildew (*Microsphaera diffusa*), pyrenochaeta leaf spot (*Pyrenochaeta glycines*), rhizoctonia aerial, foliage, and web blight (*Rhizoctonia solani*), rust (*Phakopsora pachyrhizi*), scab (*Sphaceloma glycines*), stemphylium leaf blight (*Stemphylium botryosum*), target spot (*Corynespora cassiicola*)

Fungal diseases on roots and the stem base, caused, for example, by black root rot (*Calonectria crotalariae*), charcoal rot (*Macrophomina phaseolina*), fusarium blight or wilt, root rot, and pod and collar rot (*Fusarium oxysporum, Fusarium orthoceras, Fusarium semitectum, Fusarium equiseti*), mycoleptodiscus root rot (*Mycoleptodiscus terrestris*), neocosmospora (*Neocosmospora vasinfecta*), pod and stem blight (*Diaporthe phaseolorum*), stem canker (*Diaporthe phaseolorum* var. *caulivora*), phytophthora rot (*Phytophthora megasperma*), brown stem rot (*Phialophora gregata*), pythium rot (*Pythium aphanidermatum, Pythium irregulare, Pythium debaryanum, Pythium myriotylum, Pythium ultimum*), rhizoctonia root rot, stem decay, and damping-off (*Rhizoctonia solani*), sclerotinia stem decay (*Szlerotinia sclerotiorum*), sclerotinia southern blight (*Sclerotinia rolfsii*), thielaviopsis root rot (*Thielaviopsis basicola*).

The active compound combinations according to the invention also have a potent strengthening effect in plants. They are therefore suitable for mobilizing the plants' defences against attack by unwanted microorganisms.

Plant-strengthening (resistance-inducing) substances are understood as meaning, in the present context, those substances which are capable of stimulating the defence system of plants in such a way that, when subsequently inoculated with unwanted microorganisms, the treated plants display a substantial degree of resistance to these microorganisms.

In the present case, unwanted microorganisms are understood as meaning phytopathogenic fungi, bacteria and viruses. Thus, the substances according to the invention can be employed for protecting plants against attack by the above-mentioned pathogens within a certain period of time after the treatment. The period of time within which their protection is effected is generally extended from 1 to 10 days, preferably 1 to 7 days, after the plants have been treated with the active compounds.

The fact that the active compound combinations are well tolerated by plants at the concentrations required for controlling plant diseases permits a treatment of entire plants (above-ground parts of plants and roots), of propagation stock and seed, and of the soil. The active compound combinations according to the invention can be used for foliar application or else as seed dressings.

The fact that the active compounds which can be used are well tolerated by plants at the concentrations required for controlling plant diseases permits a treatment of the seed. Accordingly, the active compounds according to the invention can be used as seed dressings.

A large part of the damage to crop plants which is caused by phytopathogenic fungi occurs as early as when the seed is attacked during storage and after the seed is introduced into the soil, as well as during and immediately after germination of the plants. This phase is particularly critical since the roots and shoots of the growing plant are particularly sensitive and even minor damage can lead to the death of the whole plant. Protecting the seed and the germinating plant by the use of suitable compositions is therefore of particularly great interest.

The control of phytopathogenic fungi which damage plants post-emergence is carried out primarily by treating the soil and the above-ground parts of plants with crop protection agents. Owing to the concerns regarding a possible impact of crop protection agents on the environment and the health of humans and animals, there are efforts to reduce the amount of active compounds applied.

The control of phytopathogenic fungi by treating the seeds of plants has been known for a long time and is subject-matter of continuous improvements. However, the treatment of seed entails a series of problems which cannot always be solved in a satisfactory manner. Thus, it is desirable to develop methods for protecting the seed and the germinating plant which dispense with the additional application of crop protection agents after sowing or after the emergence of the plants or where additional application is at least significantly reduced. It is furthermore desirable to optimize the amount of active compound employed in such a way as to provide maximum protection for the seed and the germinating plant from attack by phytopathogenic fungi, but without damaging the plant itself by the active compound employed. In particular, methods for the treatment of seed should also take into consideration the intrinsic fungicidal properties of transgenic plants in order to achieve optimum protection of the seed and the germinating plant with a minimum of crop protection agents being employed.

The present invention therefore in particular also relates to a method for the protection of seed and germinating plants from attack by phytopathogenic fungi, by treating the seed with a composition according to the invention.

The invention likewise relates to the use of the compositions according to the invention for the treatment of seed for protecting the seed and the germinating plant from phytopathogenic fungi.

Furthermore, the invention relates to seed which has been treated with a composition according to the invention so as to afford protection from phytopathogenic fungi.

One of the advantages of the present invention is that, by virtue of the particular systemic properties of the compositions according to the invention, treatment of the seed with these compositions not only protects the seed itself, but also the resulting plants after emergence, from phytopathogenic fungi. In this manner, the immediate treatment of the crop at the time of sowing or shortly thereafter can be dispensed with.

Furthermore, it must be considered as advantageous that the mixtures according to the invention can also be employed in particular in transgenic seed.

The compositions according to the invention are suitable for protecting seed of any plant variety which is employed in agriculture, in the greenhouse, in forests or in horticulture. In particular, this takes the form of seed of cereals (such as wheat, barley, rye, millet and oats), maize, cotton, soya beans, rice, potatoes, sunflowers, beans, coffee, beet (for example sugar beet and fodder beet), peanuts, vegetables (such as tomatoes, cucumbers, onions and lettuce), lawn and ornamental plants. The treatment of seed of cereals (such as wheat, barley, rye and oats), maize and rice is of particular importance.

In the context of the present invention, the composition according to the invention is applied to the seed either alone or in a suitable formulation. Preferably, the seed is treated in a state which is stable enough to avoid damage during treatment. In general, the seed may be treated at any point in time between harvest and sowing. The seed usually used has been separated from the plant and freed from cobs, shells, stalks, coats, hairs or the flesh of the fruits. Thus, for example, it is possible to use seed which has been harvested, cleaned and dried to a moisture content of below 15% by weight. Alternatively, it is also possible to use seed which, after drying, has, for example, been treated with water and then dried again.

When treating the seed, care must generally be taken that the amount of the composition according to the invention applied to the seed and/or the amount of further additives is/are chosen in such a way that the germination of the seed is not adversely affected, or that the resulting plant is not damaged. This must be borne in mind in particular in the case of active compounds which may have phytotoxic effects at certain application rates.

The compositions according to the invention can be applied directly, that is to say without comprising further components and without having been diluted. In general, it is preferable to apply the compositions to the seed in the form of a suitable formulation. Suitable formulations and methods for the treatment of seed are known to the skilled worker and are described, for example, in the following documents: U.S. Pat. No. 4,272,417 A, U.S. Pat. No. 4,245,432 A, U.S. Pat. No. 4,808,430 A, U.S. Pat. No. 5,876,739 A, US 2003/0176428 A1, WO 2002/080675 A1, WO 2002/028186 A2.

The active compound combinations according to the invention are also suitable for increasing the yield of crops. In addition, they show reduced toxicity and are well tolerated by plants.

If appropriate, the active compound combinations according to the invention can also be used in certain concentrations and application rates as herbicides, for influencing plant growth and for controlling animal pests. If appropriate, they can also be employed as intermediates and precursors for the synthesis of further active compounds.

According to the invention, it is possible to treat all plants and parts of plants. Plants are to be understood here as meaning all plants and plant populations, such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including plant cultivars which can or cannot be protected by plant breeders' certificates. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. Parts of plants also include harvested material and vegetative and generative propagation material, for example seedlings, tubers, rhizomes, cuttings and seeds.

The treatment of the plants and parts of plants according to the invention with the active compound combinations is carried out directly or by action on their environment, habitat or storage area according to customary treatment methods, for example by dipping, spraying, evaporating, atomizing, broadcasting, brushing-on and, in the case of propagation material, in particular in the case of seeds, furthermore by one- or multilayer coating.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering, if appropriate in combination with conventional methods (Genetically Modified Organisms), and parts thereof, are treated. The term "parts" or "parts of plants" or "plant parts" has been explained above.

Particularly preferably, plants of the plant cultivars which are in each case commercially available or in use are treated according to the invention.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible which exceed the effects which were actually to be expected.

The transgenic plants or plant cultivars (i.e. those obtained by genetic engineering) which are preferably to be treated according to the invention include all plants which, in the genetic modification, received genetic material which imparted particularly advantageous useful properties ("traits") to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, oilseed rape and also fruit plants (with the fruits apples, pears, citrus fruits and grapes), and particular emphasis is given to maize, soya beans, potatoes, cotton and oilseed rape. Traits that are emphasized are in particular increased defence of the plants against insects, by toxins formed in the plants, in particular those formed in the plants by the genetic material from *Bacillus thuringiensis* (for example by the genes CryIA(a), CryIA (b), CryIA(c), CryIIA, CryIIIA, CryIIIB2, Cry9c, Cry2Ab, Cry3Bb and CryIF and also combinations thereof) (hereinbelow referred to as "Bt plants"). Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), Starlink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned also include the varieties sold under the name Clearfield® (for example maize). Of course, these statements also apply to plant cultivars which have these genetic traits or genetic traits still to be developed, and which will be developed and/or marketed in the future.

Depending on their particular physical and/or chemical properties, the active compound combinations according to the invention can be converted into the customary formulations, such as solutions, emulsions, suspensions, powders, dusts, foams, pastes, soluble powders, granules, aerosols, suspoemulsion concentrates, natural and synthetic materials impregnated with active compound and microencapsulations in polymeric substances and in coating compositions for seeds, and ULV cool and warm fogging formulations.

These formulations are produced in a known manner, for example by mixing the active compounds or active compound combinations with extenders, that is liquid solvents, liquefied gases under pressure, and/or solid carriers, optionally with the use of surfactants, that is emulsifiers and/or dispersants, and/or foam formers.

If the extender used is water, it is also possible to employ, for example, organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water.

Liquefied gaseous extenders or carriers are to be understood as meaning liquids which are gaseous at standard temperature and under atmospheric pressure, for example aerosol propellants such as butane, propane, nitrogen and carbon dioxide.

Suitable solid carriers are: for example ammonium salts and ground natural minerals such as kaolins, clays, talc, chalk, quartz, attapulgite, montmorillonite or diatomaceous earth, and ground synthetic minerals such as finely divided silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignosulphite waste liquors and methylcellulose.

Tackifiers such as carboxymethylcellulose, natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other possible additives are mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The active compound content of the use forms prepared from the commercial formulations may be varied within wide ranges. The concentration of active compound of the use forms for controlling animal pests, such as insects and acarids, may be from 0.0000001 to 95% by weight of active compound and is preferably from 0.0001 to 1% by weight. Application is in a customary manner adapted to the use forms.

The formulations for controlling unwanted phytopathogenic fungi generally comprise between 0.1 and 95% by weight of active compounds, preferably between 0.5 and 90%.

The active compound combinations according to the invention can be used as such, in the form of their formulations or as the use forms prepared therefrom, such as ready-to-use solutions, emulsifiable concentrates, emulsions, suspensions, wettable powders, soluble powders, dusts and granules. They are used in a customary manner, for example by watering (drenching), drip irrigation, spraying, atomizing, broadcasting, dusting, foaming, painting, spreading-on, and as a powder for dry seed treatment, a solution for seed treatment, a water-soluble powder for seed treatment, a water-soluble powder for slurry treatment, or by encrusting etc.

The active compound combinations according to the invention can, in commercial formulations and in the use forms prepared from these formulations, be present as a mixture with other active compounds, such as insecticides, attractants, sterilants, bactericides, acaricides, nematicides, fungicides, growth regulators or herbicides.

When using the active compound combinations according to the invention, the application rates can be varied within a relatively wide range, depending on the kind of application. In the treatment of parts of plants, the application rates of active compound combination are generally between 0.1 and 10 000 g/ha, preferably between 10 and 1000 g/ha. In the treatment of seed, the application rates of active compound combination are generally between 0.001 and 50 g per kilogram of seed, preferably between 0.01 and 10 g per kilogram of seed. In the treatment of the soil, the application rates of active compound combination are generally between 0.1 and 10 000 g/ha, preferably between 1 and 5000 g/ha.

The active compound combinations can be used as such, in the form of concentrates or in the form of generally customary formulations, such as powders, granules, solutions, suspensions, emulsions or pastes.

The formulations mentioned can be prepared in a manner known per se, for example by mixing the active compounds with at least one solvent or diluent, emulsifier, dispersant and/or binder or fixative, water repellent, if desired desiccants and UV stabilizers, and, if desired, colorants and pigments and other processing auxiliaries.

The good fungicidal action of the active compound combinations according to the invention is demonstrated by the examples below. While the individual active compounds show weaknesses in their fungicidal action, the combinations show an action which exceeds a simple sum of actions.

A synergistic effect in fungicides is always present when the fungicidal activity of the active compound combinations exceeds the total of the activity of the active compounds when applied individually. The expected action for a given combination of 2 or 3 active compounds can be calculated as follows, according to S. R. Colby ("Calculating Synergistic and Antagonistic Responses of Herbicide Combinations", Weeds 1967, 15, 20-22):

If

X is the efficacy when employing active compound A at an application rate of m g/ha, Y is the efficacy when employing active compound B at an application rate of n g/ha, Z is the efficacy when employing active compound C at an application rate of r g/ha, $E_1$ is the efficacy when employing active compounds A and B at application rates of m and n g/ha and $E_2$ is the efficacy when employing active compounds A and B and C at application rates of m and n and r g/ha, then $$E_1 = X + Y - \frac{X \cdot Y}{100}$$

and for a combination of 3 active compounds:

$$E_2 = X + Y + Z - \left(\frac{X \cdot Y + X \cdot Z + Y \cdot Z}{100}\right) + \frac{X \cdot Y \cdot Z}{10000}$$

Here, the efficacy is determined in %. 0% means an efficacy which corresponds to that of the control, whereas an efficacy of 100% means that no infection is observed.

If the actual fungicidal activity exceeds the calculated value, the activity of the combination is superadditive, i.e. a synergistic effect is present. In this case, the actually observed efficacy must exceed the value calculated using the above formula for the expected efficacies $E_1$ and $E_2$.

The invention is illustrated by the examples below. However, the invention is not limited to the examples.

USE EXAMPLES

Example A

*Fusarium graminearum* Test (Barley)/Curative

Solvent: 50 parts by weight of N,N-dimethylacetamide

Emulsifier: 1 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for curative activity, young plants are sprayed with a conidia suspension of *Fusarium graminearum*. The plants remain in an incubation cabin at 20° C. and 100% relative atmospheric humidity for 24 hours. The plants are then sprayed with the preparation of active compound at the stated application rate. After the spray coating has dried on, the plants remain in a greenhouse under transparent incubation hoods at a temperature of about 20° C. and a relative atmospheric humidity of about 100%.

Evaluation is carried out 7 days after the inoculation. What is determined is the efficacy in %. 0% means an efficacy which corresponds to that of the control, whereas an efficacy of 100% means that no infection is observed.

TABLE A

*Fusarium graminearum* test (barley)/curative

| Active compounds | Active compound application rate in g/ha | Efficacy in % found* | Efficacy in % calc.** |
|---|---|---|---|
| (I-2) N-[2-(1,3-dimethyl-butyl)phenyl]-5-fluoro-1,3-dimethyl-1H-pyrazole-4-carboxamide | 125 | 42 | |
| (II-15) prothioconazole | 125 | 58 | |
| (III-2) fluoxastrobin | 125 | 50 | |
| (I-2) + (II-15) 1:1 | 125 + 125 | 75 | 76 |
| (I-2) + (III-2) 1:1 | 125 + 125 | 67 | 71 |
| (II-15) + (III-2) 1:1 | 125 + 125 | 67 | 79 |
| (I-2) + (II-15) + (III-2) 1:1:1 | 125 + 125 + 125 | 92 | 88 |

*found = activity found
**calc. = activity calculated using Colby's formula

Example B

*Erysiphe* Test (Wheat)/Curative

Solvent: 50 parts by weight of N,N-dimethylacetamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for curative activity, young plants are sprayed with spores of *Erysiphe graminis* f.sp. *tritici*. 48 hours after the inoculation, the plants are sprayed with the preparation of active compound at the stated application rate. The plants are placed in a greenhouse at a temperature of about 20° C. and a relative atmospheric humidity of about 80% to promote the development of mildew pustules.

Evaluation is carried out 8 days after the inoculation. What is determined is the efficacy in %. 0% means an efficacy which corresponds to that of the control, whereas an efficacy of 100% means that no infection is observed.

TABLE B

*Erysiphe* test (wheat)/curative

| Active compounds | Active compound application rate in g/ha | Efficacy in % found* | Efficacy in % calc.** |
|---|---|---|---|
| (I-2) N-[2-(1,3-dimethyl-butyl)phenyl]-5-fluoro-1,3-dimethyl-1H-pyrazole-4-carboxamide | 125 | 0 | |
| (II-15) prothioconazole | 125 | 33 | |
| (III-2) fluoxastrobin | 125 | 39 | |
| (I-2) + (II-15) 1:1 | 125 + 125 | 22 | 33 |
| (I-2) + (III-2) 1:1 | 125 + 125 | 61 | 39 |
| (II-15) + (III-2) 1:1 | 125 + 125 | 72 | 59 |
| (I-2) + (II-15) + (III-2) 1:1:1 | 125 + 125 + 125 | 83 | 59 |

*found = activity found
**calc. = activity calculated using Colby's formula

Example C

*Penicillium brevicaule*-Test (In Vitro)/Microtest

The microtest was performed in liquid medium with potato-dextrose broth (PDB) using microtitre plates.

The active compound is applied as the technical active substance dissolved in aceton.

A spore suspension of *Penicillium brevicaule* was used for inoculation. After 4 days of incubation by darkness under shaking (10 Hrz), the optical density in each cavity was evaluated with the aid of a microtitre plate reader.

0% means an efficacy which corresponds to that of the control, while an efficacy of 100% means that no fungal growth is observed.

The table below clearly shows that the observed activity of the active compound combination according to the invention is greater than the calculated activity, i.e. a synergistic effect is present.

TABLE C

*Penicillium brevicaule* -Test (in vitro)/Microtest

| Active compound | Rate of application of active compound in ppm | Efficacy in % |
|---|---|---|
| (I-2) N-[2-(1,3-dimethyl-butyl)phenyl]-5-fluoro-1,3-dimethyl-1H-pyrazole-4-carboxamide | 0.03 | 16 |
| (III-4) Trifloxystrobin | 0.003 | 1 |
| (II-18) Ipconazole | 0.003 | 8 |

| Compound combination | | Act* | Exp** |
|---|---|---|---|
| (II-18) + (III-4) | 0.03 + 0.003 | 21 | 17 |
| (II-18) + (I-2) | 0.03 + 0.003 | 24 | 23 |
| (III-4) + (I-2) | 0.003 + 0.003 | 21 | 9 |
| (II-18) + (III-4) + (I-2) | 0.03 + 0.003 + 0.003 | 29 | 23 |

*Act = actual efficacy (%)
**Exp. = Expected value, calculated using Colby's formula

Example D

*Pyrenophora teres* (Barley)-Test/Curative

Solvent: 50 parts by weight of N,N-dimethylacetamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration or the active compound or a combination of active compounds in a commercially available formulation is diluted with water to the desired concentration.

To test for curative activity, young plants are sprayed with a conidia suspension of *Pyrenophora teres*. The plants remain for 48 hours in an incubation cabinet at 20° C. and a relative atmospheric humidity of 100% and are then sprayed with the preparation of active compound at the stated rate of application.

The plants are placed in a greenhouse at a temperature of approximately 20° C. and a relative atmospheric humidity of approximately 80%.

The test is evaluated 8 days after the inoculation.

The good fungicidal activity of the active compound combinations according to the invention is evident from the example below. While the individual active compounds exhibit weaknesses with regard to the fungicidal activity, the combinations have an activity which exceeds a simple addition of activities.

TABELLE D

*Pyrenophora teres*-Test (Gerste)/kurativ

| Active compound | Rate of application of active compound in g/ha | Efficacy in % |
|---|---|---|
| (I-2) N-[2-(1,3-dimethylbutyl)phenyl]-5-fluoro-1,3-dimethyl-1H-pyrazol-4-carboxamide | 50 | 22 |
| (I-23) N-(3',4'-dichloro-5-fluoro-1,1'-biphenyl-2-yl)-3-(difluoromethyl)-1-methyl-1H-pyrazol-4-carboxamide | 50 | 22 |
| (II-15) prothioconazole | 50 | 22 |
| (II-17) tebuconazole | 50 | 22 |
| (III-2) fluoxastrobin | 50 | 22 |

| Compound combination | | Act* | Exp** |
|---|---|---|---|
| (I-2) + (II-15) | 50 + 50 | 44 | 39 |
| (I-2) + (III-2) | 50 + 50 | 67 | 39 |
| (II-15) + (III-2) | 50 + 50 | 56 | 39 |
| (I-23) + (II-15) | 50 + 50 | 56 | 39 |
| (I-23) + (II-17) | 50 + 50 | 56 | 39 |
| (II-15) + (II-17) | 50 + 50 | 56 | 39 |
| (I-2) + (II-15) + (III-2) | 50 + 50 + 50 | 78 | 53 |
| (I-23) + (II-15) + (II-17) | 50 + 50 + 50 | 78 | 53 |

*Act = actual efficacy (%)
**Exp. = Expected value, calculated using Colby's formula

The invention claimed is:

1. A composition comprising a synergistically effective amount of (I-23) N-(3',4'-dichloro-5-fluoro-1,1'-biphenyl-2-yl)-3-(difluoromethyl)-1-methyl-1H-pyrazole-4-carboxamide, (II-15) prothioconazole and (III-2) fluoxastrobin, wherein 0.1 to 10 parts by weight of (II-15) prothioconazole and 0.1 to 10 parts by weight of (III-2) fluoxastrobin are present per 1 part by weight of (I-23) N-(3',4'-dichloro-5-fluoro-1,1'-biphenyl-2-yl)-3-(difluoromethyl)-1-methyl-1H-pyrazole-4-carboxamide.

2. The composition according to claim 1 further comprising seed.

3. The composition according claim 1 further comprising extenders and/or surfactants.

4. The composition according to claim 1, wherein the weight ratio of said (I-23), (II-15) and (III-2) is 1:1:1.

5. A method for controlling unwanted phytopathogenic fungi comprising applying the composition according to claim 1 to said unwanted phytopathogenic fungi and/or a habitat thereof and/or a seed.

6. The method according to claim 5 wherein the habitat further comprises a plant.

7. The method according to claim 6 wherein the plant is a transgenic plant.

8. The method according to claim 5 wherein the seed is seed of a transgenic plant.

9. A process to prepare a fungicidal composition comprising mixing the composition according to claim 1 with extenders and/or surfactants.

* * * * *